(12) United States Patent
Kim

(10) Patent No.: US 12,064,586 B2
(45) Date of Patent: Aug. 20, 2024

(54) END CAP FOR MEDICAL LIQUID INJECTION APPARATUS AND MEDICAL LIQUID INJECTION APPARATUS SET

(71) Applicant: Yong Hyun Kim, Gyeonggi-do (KR)

(72) Inventor: Yong Hyun Kim, Gyeonggi-do (KR)

( * ) Notice: Subject to any disclaimer, the term of this patent is extended or adjusted under 35 U.S.C. 154(b) by 835 days.

(21) Appl. No.: 17/260,817

(22) PCT Filed: Jul. 26, 2019

(86) PCT No.: PCT/KR2019/009338
§ 371 (c)(1),
(2) Date: Jan. 15, 2021

(87) PCT Pub. No.: WO2020/027507
PCT Pub. Date: Feb. 6, 2020

(65) Prior Publication Data
US 2021/0268257 A1    Sep. 2, 2021

(30) Foreign Application Priority Data

Aug. 1, 2018    (KR) .......................... 10-2018-0090005

(51) Int. Cl.
*A61M 39/20* (2006.01)
*A61M 5/142* (2006.01)
*A61M 5/165* (2006.01)
*A61M 5/14* (2006.01)

(52) U.S. Cl.
CPC ............ *A61M 39/20* (2013.01); *A61M 5/142* (2013.01); *A61M 5/165* (2013.01); *A61M 2005/1402* (2013.01); *A61M 2205/7527* (2013.01)

(58) Field of Classification Search
CPC ........ A61M 2005/1402; A61M 5/3146; A61M 5/142; A61M 39/20
See application file for complete search history.

(56) References Cited

U.S. PATENT DOCUMENTS 5,853,386 A    12/1998   Davis et al.
6,110,153 A    8/2000    Davis et al.
(Continued)

FOREIGN PATENT DOCUMENTS

CN    104271043 A    1/2015
CN    107636370 A    1/2018
(Continued)

*Primary Examiner* — Emily L Schmidt
*Assistant Examiner* — Samuel J Marrison
(74) *Attorney, Agent, or Firm* — Clark Hill PLC; James R. Foley

(57) ABSTRACT

An end cap according to a disclosed embodiment is connected to a downstream side of a flow path of a medical liquid injection apparatus and is configured such that a priming liquid is introduced into the end cap. The end cap includes: a refraction part formed of a transparent material having a refractive index ($n_r$) greater than 1 and including a first surface and a second surface forming an internal angle smaller than 90 degrees; and an indication part disposed to be spaced apart from the second surface. The end cap forms a passage in which the introduced priming liquid is movable, and a part of the passage is located between the second surface and the indication part.

12 Claims, 15 Drawing Sheets

(56) References Cited

U.S. PATENT DOCUMENTS

| | | | |
|---|---|---|---|
| 2005/0203460 A1* | 9/2005 | Kim | A61M 39/20 604/126 |
| 2008/0114301 A1* | 5/2008 | Bandhauer | A61M 1/73 604/20 |
| 2009/0009764 A1 | 1/2009 | Slepicka | |
| 2009/0128803 A1 | 5/2009 | Gan | |
| 2010/0063445 A1* | 3/2010 | Sternberg | A61M 39/20 604/404 |
| 2011/0071480 A1* | 3/2011 | Katerkamp | A61M 25/0693 604/272 |
| 2012/0145729 A1 | 6/2012 | Holger et al. | |
| 2012/0209111 A1* | 8/2012 | Cowan | A61M 5/1452 600/432 |
| 2013/0125808 A1 | 5/2013 | Sternberg et al. | |
| 2017/0065770 A1 | 3/2017 | Cowan et al. | |
| 2017/0304545 A1 | 10/2017 | Blei et al. | |
| 2018/0050187 A1 | 2/2018 | Kunschak et al. | |

FOREIGN PATENT DOCUMENTS

| | | |
|---|---|---|
| JP | 2001-523120 A | 11/2001 |
| JP | 2011-517597 A | 6/2011 |
| JP | 2012-501798 A | 1/2012 |
| JP | 2017-517347 A | 6/2017 |
| KR | 10-2011-0059637 A | 6/2011 |
| WO | 2010/030602 A1 | 3/2010 |
| WO | 2017/046179 A1 | 3/2017 |

\* cited by examiner

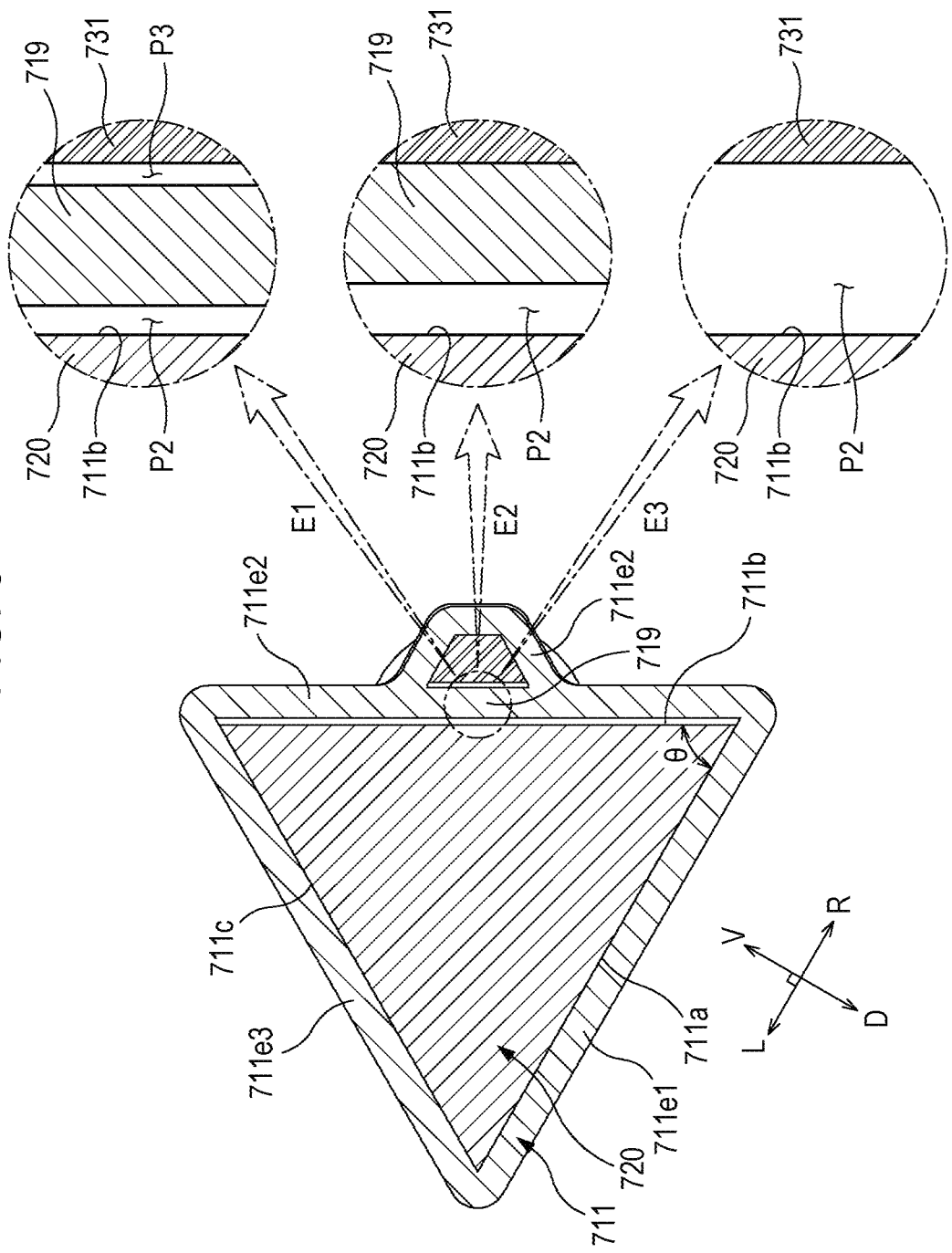

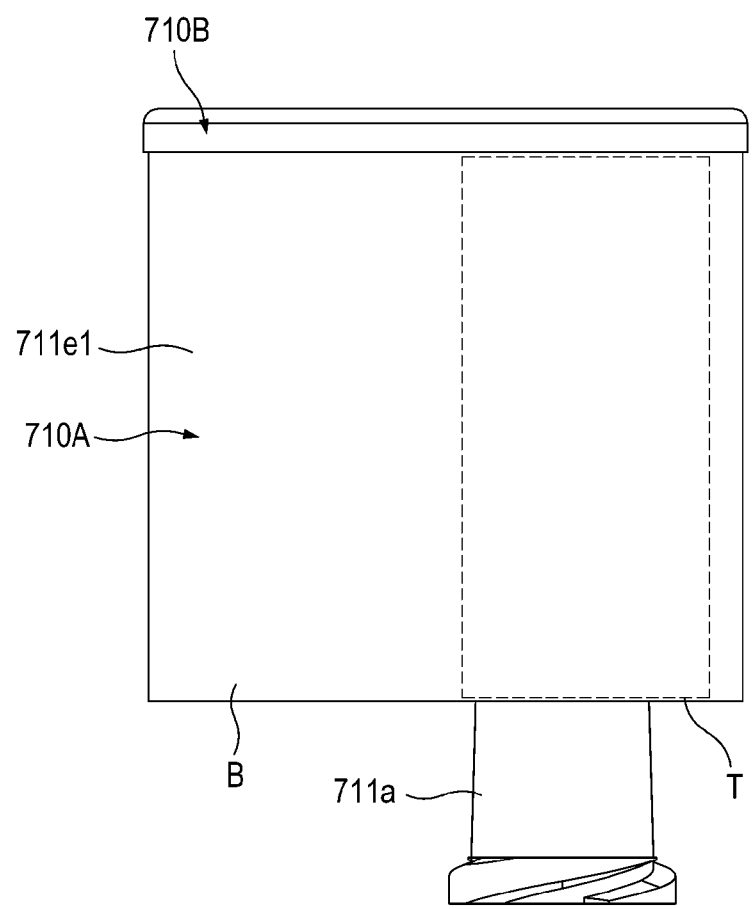
[Fig. 7A]

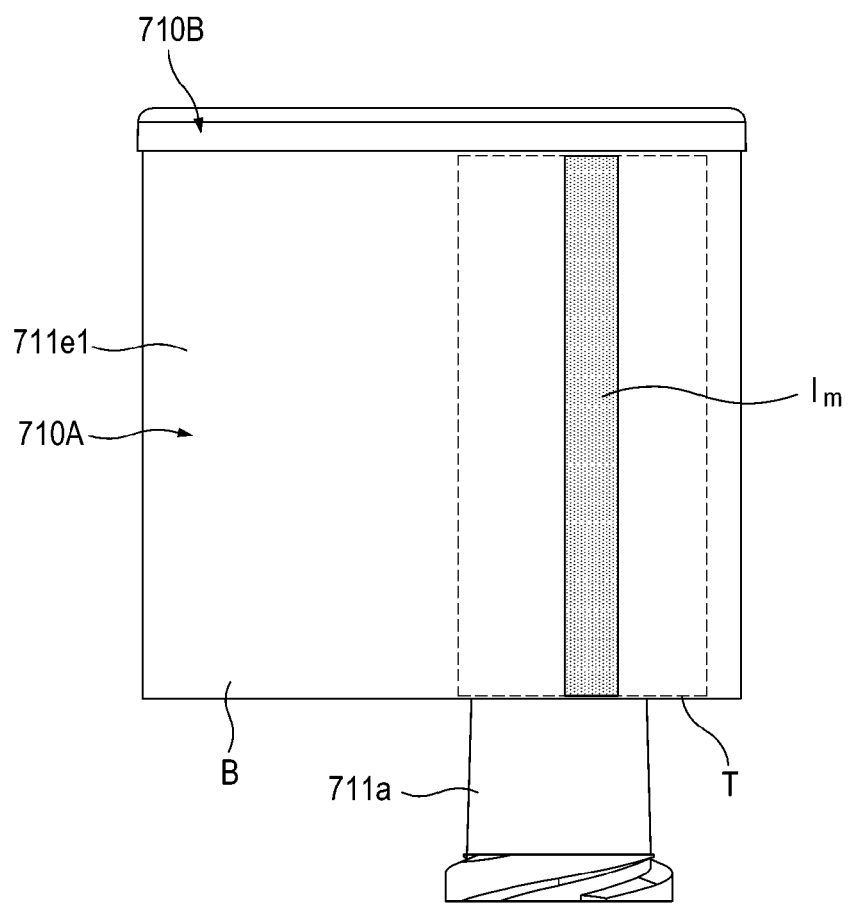
[Fig. 7B]

[Fig. 8]
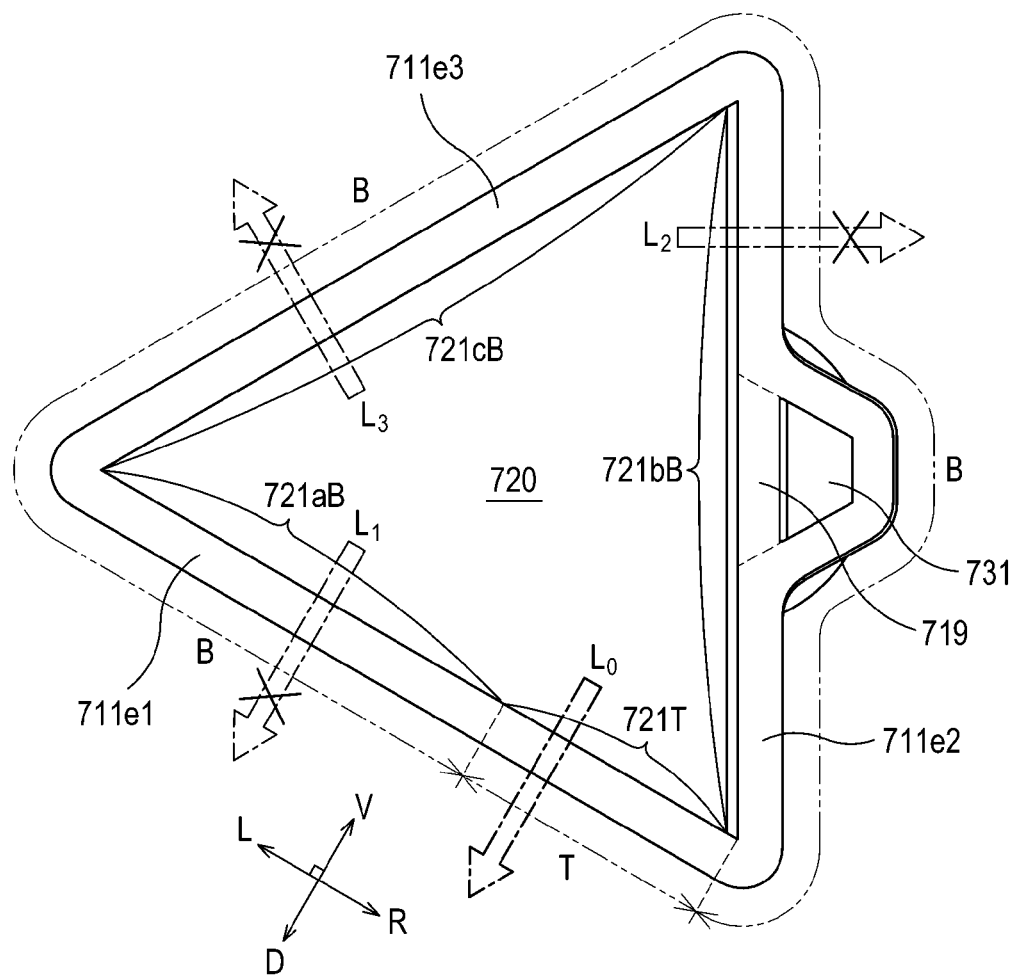

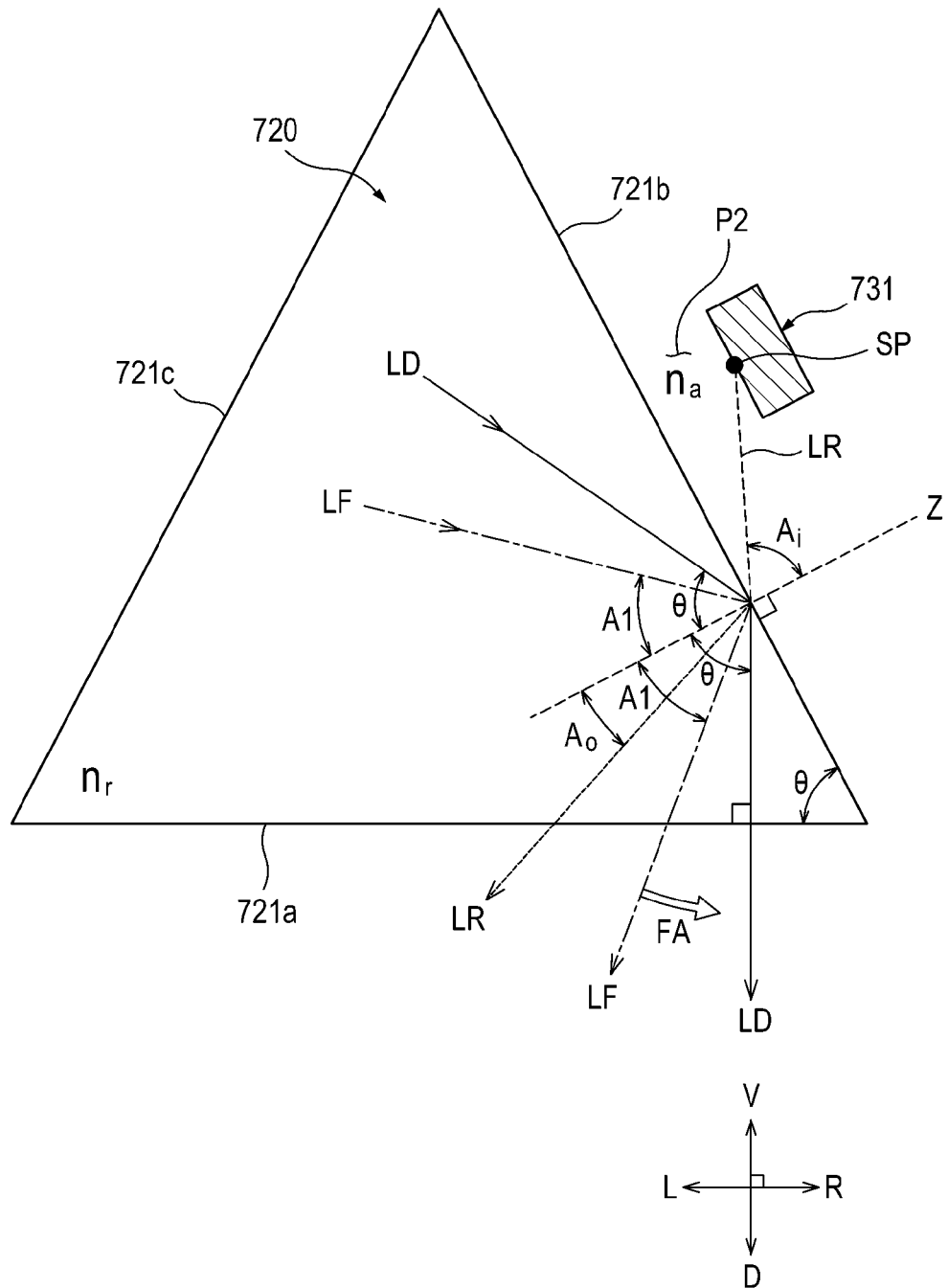
[Fig. 9A]

[Fig. 9B]
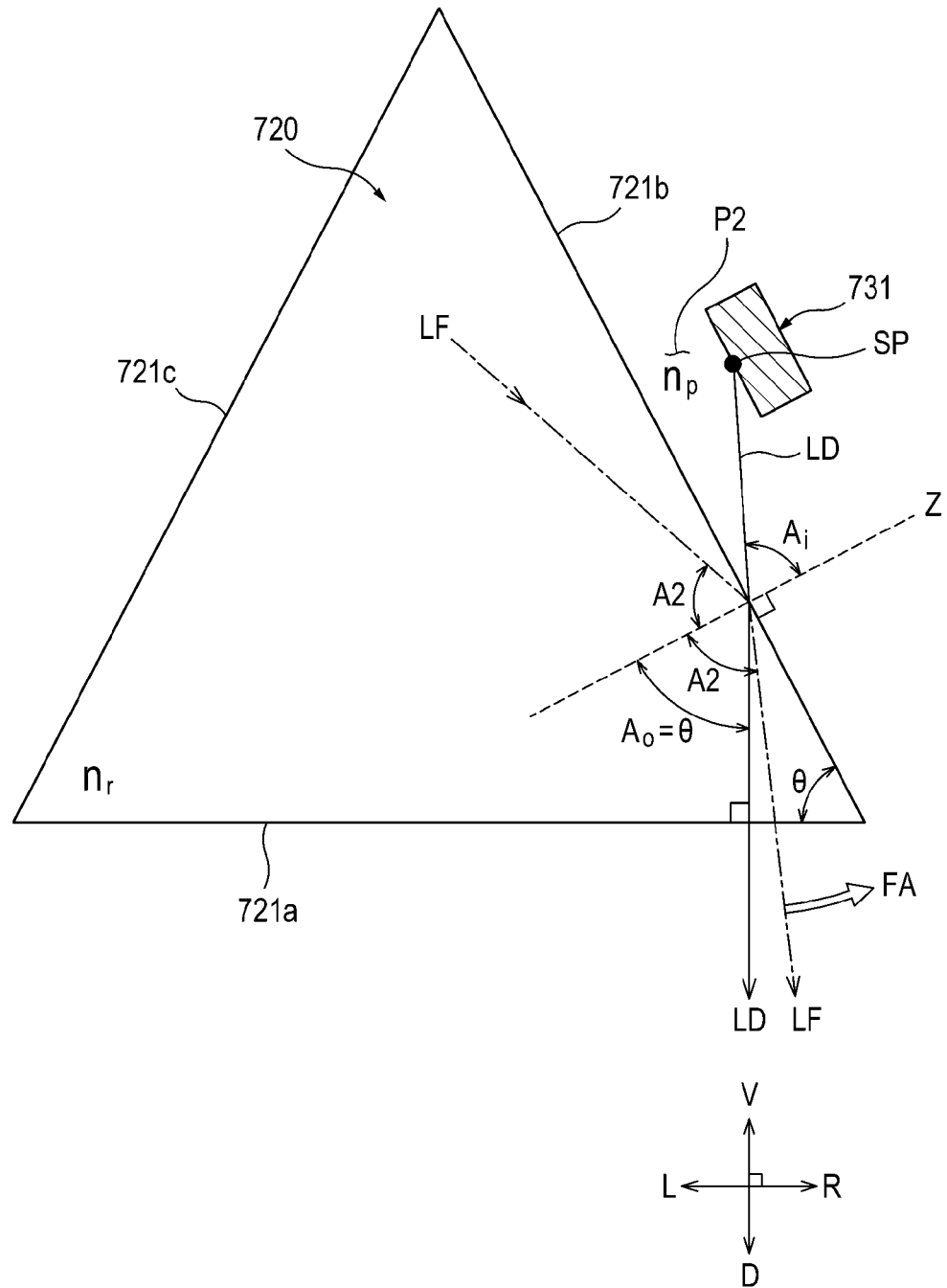

[Fig. 9C]
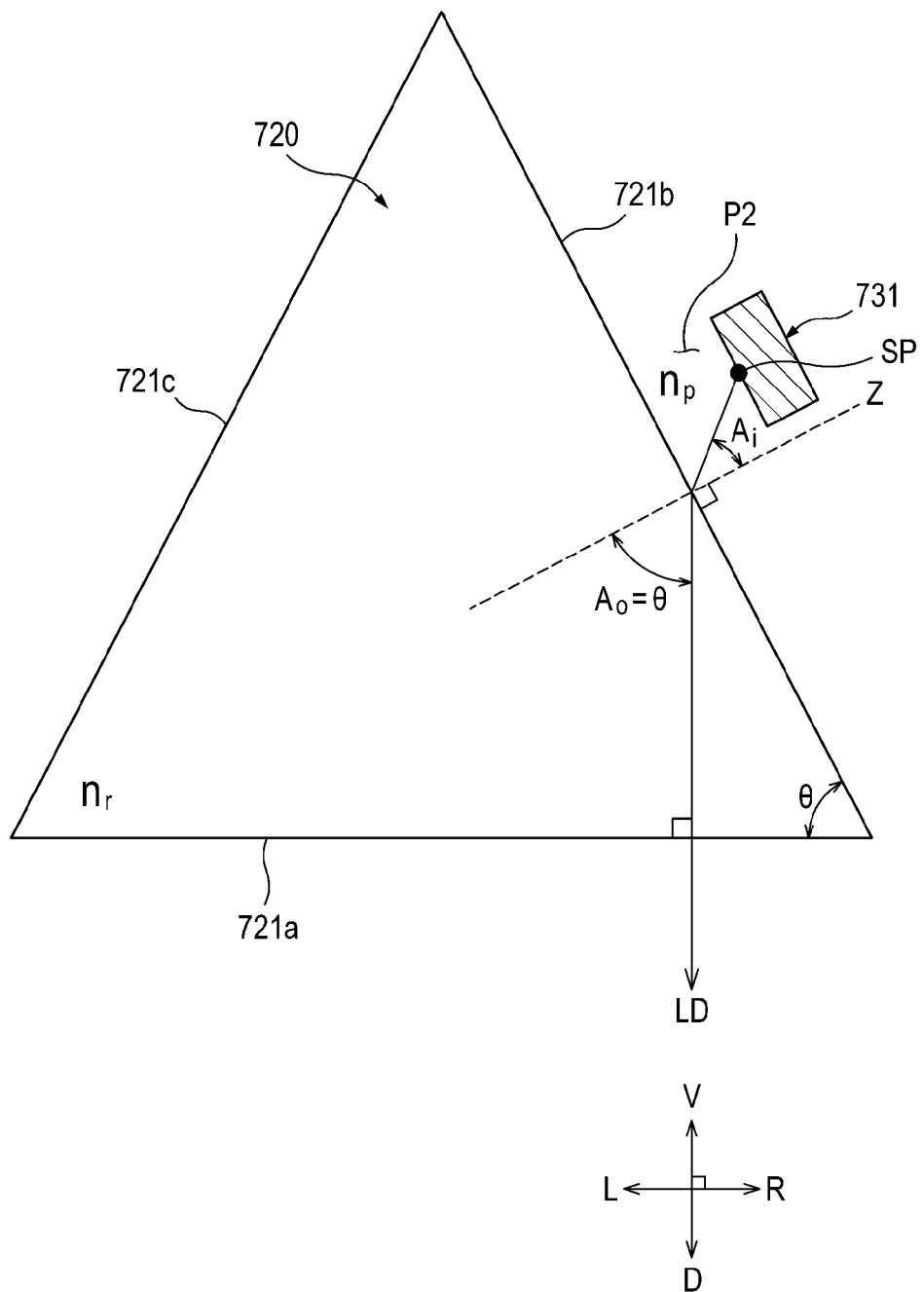

[Fig. 10]
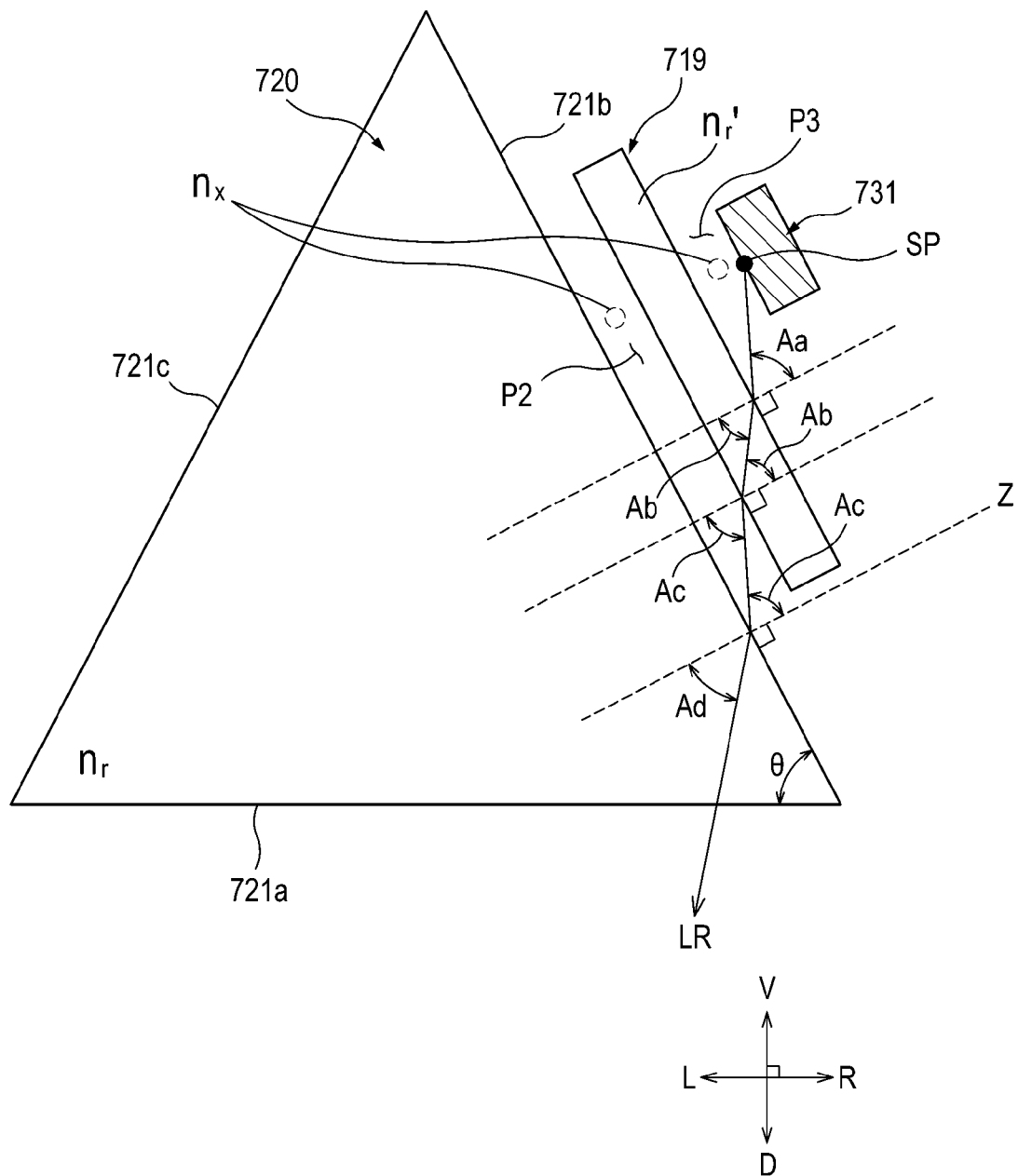

[Fig. 11]
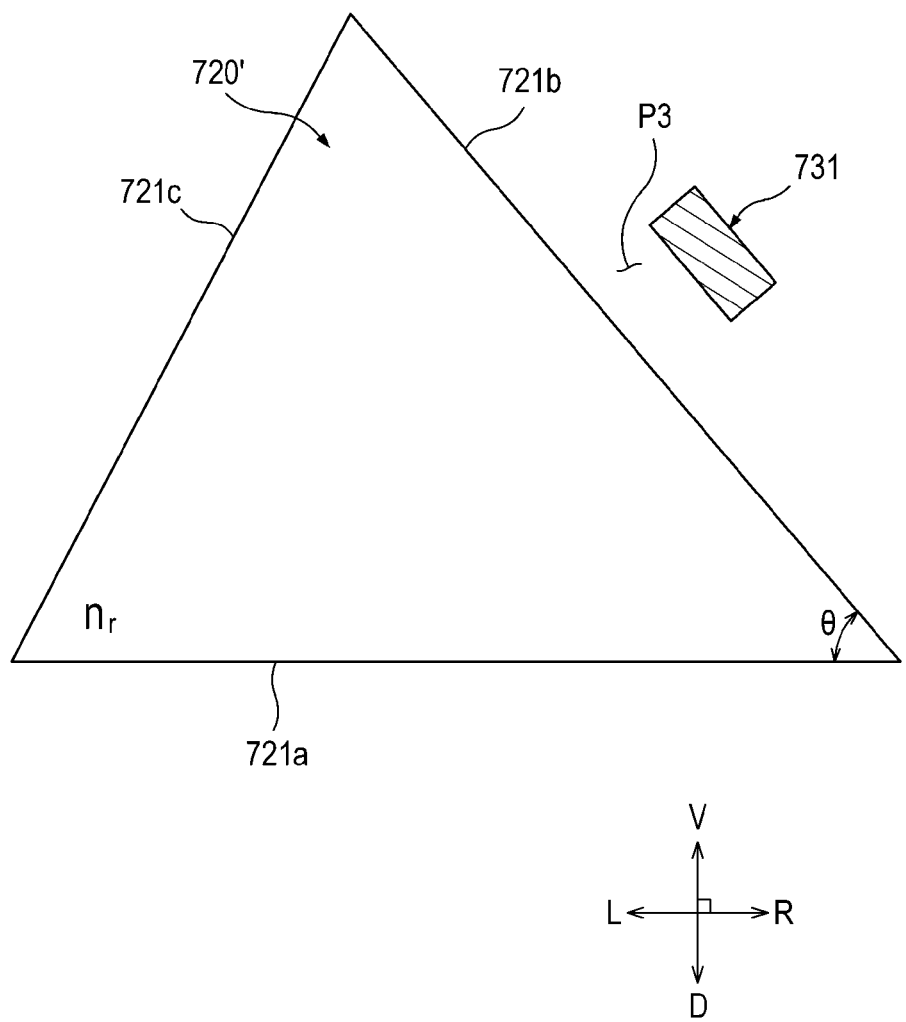

[Fig. 12]
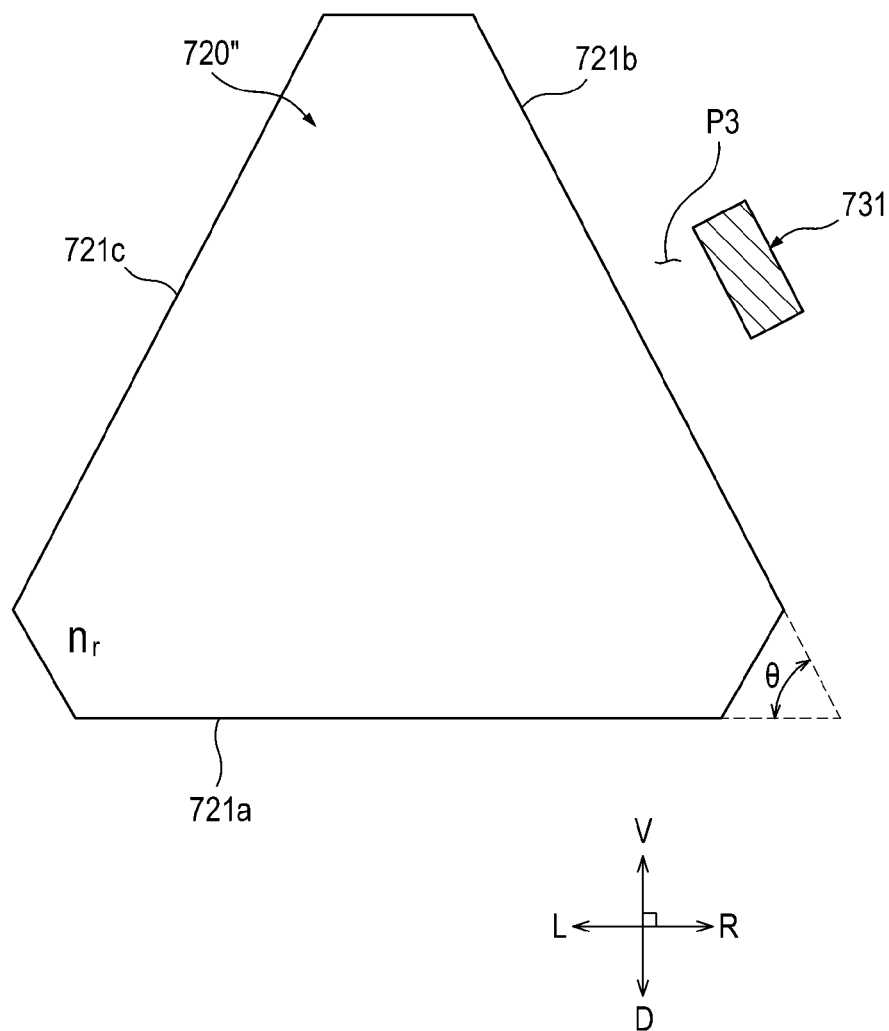

END CAP FOR MEDICAL LIQUID INJECTION APPARATUS AND MEDICAL LIQUID INJECTION APPARATUS SET

TECHNICAL FIELD

The present disclosure relates to a medical apparatus for injecting a medical liquid and an end cap for a medical liquid injection apparatus.

BACKGROUND ART

There is known a medical liquid injection device for injecting a liquid drug into a patient in order to supply the liquid drug thereto. The medical liquid in a prede-termined storage space moves through a flow path and flows into a patient's body using the above-described medical liquid injection apparatus.

There is known a priming operation for filling the inside of a flow path, in which the medical liquid is to move, with a priming liquid (e.g., a medical liquid or a saline solution to be injected) before a member to be connected to the patient, such as a catheter or an injection needle, is coupled in order to prevent air from flowing into the patient's body during the use of the medical liquid injection apparatus.

In this priming operation, an end cap is connected to an end of the flow path in which the medical liquid is to move in order to help remove the air in the flow path. In the state in which the end cap is connected to the flow path, the priming liquid fills the flow path and then fills the space inside the end cap. Then, the end cap is separated from the flow path, and the member to be connected to the patient is coupled to the flow path and is used.

DISCLOSURE OF INVENTION

Technical Problem

Conventionally, it is difficult to visually confirm whether the priming liquid has reached the end cap through the flow path of the medical liquid injection apparatus. Particularly, when the priming liquid is transparent, it is inconvenient to pay particular attention in confirming whether the priming liquid has reached the end cap. Embodiments of the present disclosure solve the problems of the prior art described above.

Conventionally, it is necessary for a medical staff (e.g., a doctor or a nurse) to constantly watch and observe the priming liquid while the priming liquid is reaching the end cap through the flow path of the medical liquid injection apparatus. Embodiments of the present disclosure solve the problems of the prior art described above.

Solution to Problem

An aspect of the present disclosure provides embodiments of an end cap connected to a downstream side of a flow path of a medical liquid injection apparatus and configured such that a priming liquid is introduced into the end cap. An end cap for a medical liquid injection apparatus according to a representative embodiment includes a refraction part formed of a transparent material having a refractive index $n_r$ greater than 1 and including a first surface and a second surface forming an internal angle $\theta$ smaller than 90 degrees; and an indication part disposed to be spaced apart from the second surface. The end cap forms a passage in which the intro-duced priming liquid is movable. A part of the passage is located between the second surface and the indication part.

The refraction part may be configured such that, in a first state in which the passage is filled with air, all light that starts from the indication part travels in a direction different from a display direction, which is an outward direction perpen-dicular to the first surface, and, in a second state in which the passage is filled with the priming liquid, a part of light that starts from the indication part travels in the display direction.

The refraction part may be configured such that, in the first state, light totally reflected from the second surface travels in the display direction and, in the second state, a part of light that starts from the indication part is refracted on the second surface so as to travel in the display direction.

A transparent portion may be formed in the end cap to transmit light traveling in the display direction to the out-side.

A blind portion may be formed in the end cap to block, scatter, or transmit, with transparency lower than transpar-ency of the transparent portion, light passing through an area, other than an area corresponding to the transparent portion, in a peripheral surface of the refraction part includ-ing the first surface and the second surface.

The transparent portion may be configured to correspond to a specific area in the first surface. The specific area may be located in a direction of the internal angle $\theta$ that the first surface forms with the second surface with respect to an area, other than the specific area, in the first surface.

The internal angle $\theta$ may equal to or greater than $$\sin^{-1}\left(\frac{1}{n_r}\right).$$

When the priming liquid has a refractive index $n_p$, the refractive index $n_r$ may be equal to or greater than $$\frac{1}{\sin\theta}$$

and smaller than $$\frac{n_p}{\sin\theta}.$$

The refractive index $n_r$ may be equal to or greater than $$\frac{1}{\sin\theta}$$

and smaller than $$\frac{1.333}{\sin\theta}.$$

The end cap may further include an auxiliary refraction part formed of a transparent material having a refractive index $n_r'$ greater than 1 and located between the second surface and the indication part, the auxiliary refraction part being disposed to be spaced apart from the second surface. A part of the passage may be located between the second surface and the auxiliary refraction part.

The refractive index $n_r'$ may be greater than 1.333.

The end cap may further include a casing part having an inlet port configured to allow the liquid to be introduced into the end cap therethrough from the flow path, and an outlet port configured to allow air to flow out from an inside of the passage therethrough. The refraction part may be disposed inside the casing part.

A surface, other than the second surface, in a peripheral surface of the refraction part comprising the first surface and the second surface, may be in contact with an inner surface of the casing part.

The end cap may further include: a liquid absorption part disposed in a downstream side of a part of the passage located between the second surface and the indication part and configured to absorb the liquid; and a hydrophobic filter part disposed on a downstream side of the liquid absorption part, and configured to allow air to pass therethrough.

Another aspect of the present disclosure provides embodiments of a medical liquid injection apparatus set. The medical liquid injection apparatus set includes: a pumping module configured to pressurize a medical liquid: a connection flow path connected to the pumping module on an upstream side thereof and configured to guide a flow of a priming liquid; and an end cap connected to a downstream side of the connection flow path and configured such that the priming liquid is introduced into the end cap. The end cap comprises: a refraction part formed of a transparent material having a refractive index $n_r$ greater than 1 and including a first surface and a second surface that forms an internal angle θ smaller than 90 degrees: and an indication part disposed to be spaced apart from the second surface. The end cap forms a passage in which the introduced priming liquid is movable. A part of the passage is located between the second surface and the indication part.

Advantageous Effects of Invention

According to embodiments of the present disclosure, it is possible to visually recognize in an easy and quick manner that the priming liquid has been completely introduced into the end cap, and it is possible to significantly reduce the probability of a mistake occurring by a medical staff in determining whether the priming liquid has been completely introduced into the end cap.

According to an embodiment of the present disclosure, it is possible to visually confirm a display change before and after the introduction of the priming liquid using a naked eye. Further, since the display change is configured using a physical optical property, rather than using a chemical substance reaction, the possibility of con-tamination of a liquid, which may be introduced into a human body, is remarkably low.

BRIEF DESCRIPTION OF DRAWINGS

FIG. 6 illustrates a horizontal cross-sectional view of the end cap 700 of FIG. 2, taken along line S2-S2' and partially enlarged views taken according to a first embodiment (E1), a second embodiment (E2), and a third embodiment (E3).

FIGS. 7A and 7B are elevation views of the end cap 700 of FIG. 6 viewed in an observation direction V, in which FIG. 7A is a view illustrating a state before a priming liquid is introduced into the end cap 700 and FIG. 7B is a view illustrating a state after the end cap 700 is filled with the priming liquid.

FIG. 8 is a cross-sectional view illustrating FIG. 6 without hatching, showing a transparent portion T and a blind portion B.

FIGS. 9A to 9C are conceptual cross-sectional views taken by horizontally cutting a refraction part 720 and an indication part 731 in an embodiment in which an auxiliary refraction part 719 is not provided, in which FIG. 9A illustrates exemplary light traveling paths in the state in which a main passage portion P2 is filled with air and FIGS. 9B and 9C illustrates exemplary light traveling paths in the state in which the main passage portion P2 is filled with the priming liquid.

FIG. 10 is a conceptual cross-sectional view taken by horizontally cutting a refraction part 720, an auxiliary refraction part 719, and an indication part 731 in an embodiment in which the auxiliary refraction part 719 is provided, in which an exemplary light traveling path is illustrated.

FIG. 10 is a conceptual cross-sectional view taken by horizontally cutting a refraction part 720, an auxiliary refraction part 719, and a indication part 731 in an embodiment in which the auxiliary refraction part 719 is provided, in which an exemplary light traveling path is illustrated.

FIG. 11 is a conceptual cross-sectional view obtained by horizontally cutting a refraction part 720' according to another embodiment.

FIG. 12 is a conceptual cross-sectional view obtained by horizontally cutting a refraction part 720" according to still another embodiment.

MODE FOR THE INVENTION

Figure 1:
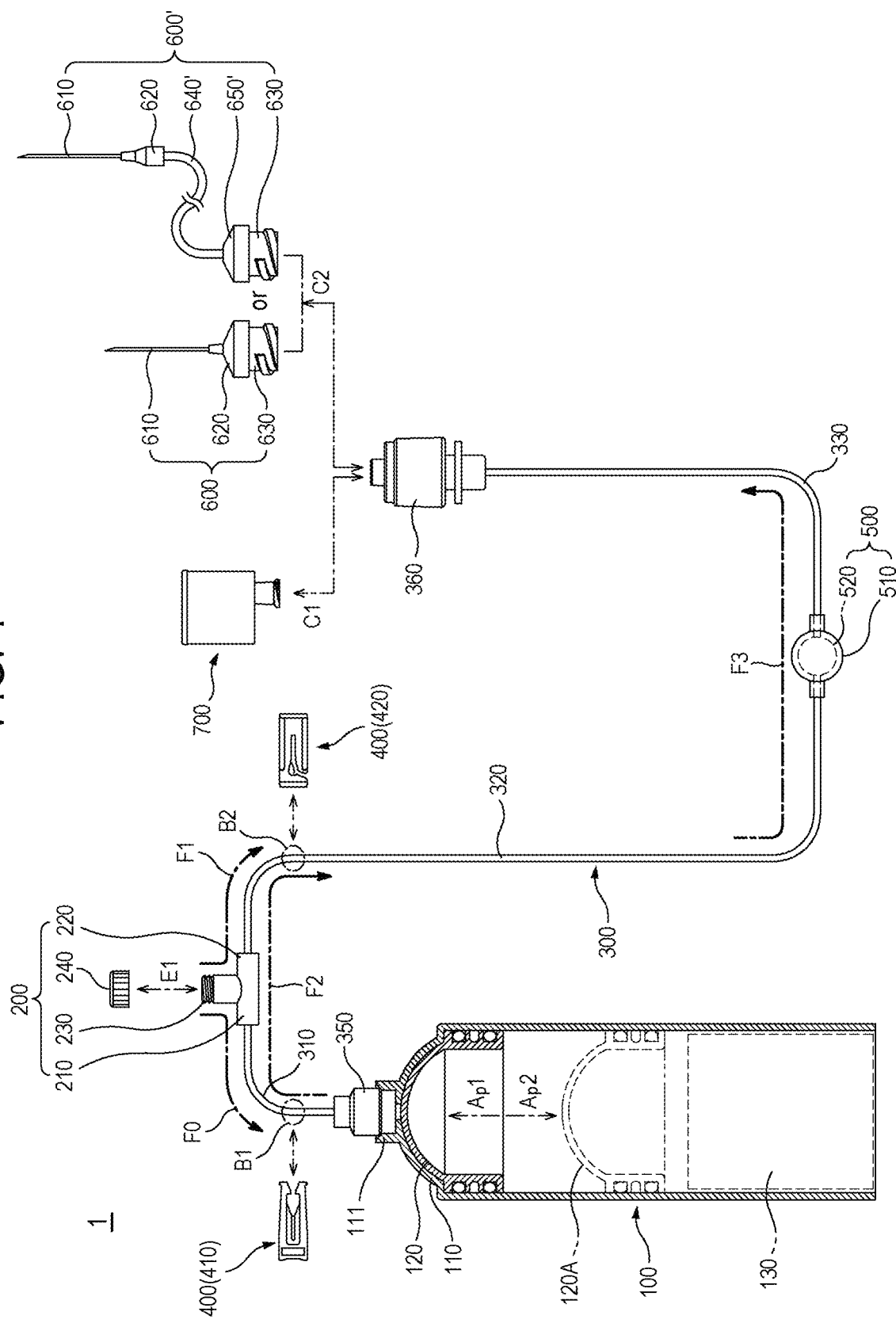
FIG. 1 is a conceptual view showing an entire medical liquid injection apparatus set 1 according to an embodiment of the present disclosure.

Embodiments of the present disclosure are exemplified for the purpose of describing the technical idea of the present disclosure. The scope of the present disclosure is not limited to the embodiments represented below or to the detailed description of the embodiments.

All technical and scientific terms used in the present disclosure have the meaning commonly understood by a person ordinarily skilled in the art to which the present disclosure belongs unless otherwise defined. All the terms used in the present disclosure are selected for the purpose of more clearly describing the present disclosure, but are not selected to limit the scope of the present disclosure.

As used in this disclosure, the terms, such as "including", "comprising", and "having", should be understood as open-ended terms that imply the possibility of including other embodiments unless otherwise mentioned in a phrase or sentence in which the terms are contained.

A singular term used in the present disclosure may include plural meanings unless otherwise mentioned, which is equally applicable to a singular term set forth in the claims.

Terms such as "first" and "second" are used in order to distinguish a plurality of components from one another, and do not limit the order or importance of the corresponding components.

In the present disclosure, when an element is referred to as being "connected" or "coupled" to another element, it is to be understood that the element may be directly connected or coupled to the other element, or may be connected or coupled via another new another component.

Hereinafter, embodiments of the present disclosure will be described with reference to the accompanying drawings. In the accompanying drawings, a prime symbol (') or a double prime symbol (") may be indicated after the reference numerals in order to distinguish different embodiments. In addition, in the accompanying drawings, the same or corresponding components are denoted by the same reference numerals. In the following description of the embodiments, duplicate descriptions for the same or corresponding components may be omitted. However, even if the descriptions of components are omitted, such components are not intended to be included in any embodiment.

Hereinafter, a medical liquid injection apparatus set 1 according to an embodiment of the present disclosure will be described with reference to FIG. 1. The medical liquid injection apparatus set 1 includes a medical liquid injection apparatus 100, 300 configured to pressurize a medical liquid and to guide the flow, and an end cap 700 configured to be connected to a flow path 300 of the medical liquid injection ap-paratuses 100, 300. The medical liquid injection apparatus 100, 300 includes a pumping module 100 configured to pressurize the medical liquid and a connection flow path 300 configured to guide the medical liquid. In response to the pressurization in the pumping module 100, the medical liquid flowing out from the pumping module 100 flows through the connection flow path 300.

The medical liquid injection apparatus set 1 may include a port module 200 disposed on the connection flow path 300. The port module 200 is configured such that the inside of the pumping module 100 is able to be filled with a liquid (e.g., a medical liquid or saline solution). The liquid introduced through the port module 200 may be introduced into the pumping module 100.

The medical liquid injection apparatus set 1 may include a connection pipe opening and closing module 400 configured to change whether or not at least one point of the connection flow passage 300 is opened. The medical liquid injection apparatus set 1 may include a filter module 500 configured to filter out foreign matter of liquid flowing in the connection flow path 300.

The medical liquid injection apparatus set 1 includes a patient connection module 600 or 600' configured to inject a medical liquid into a patient. The patient connection module 600 or 600' includes a component introduced into the patient's body, such as an injection needle 610.

The patient connection module 600 or 600' may include an introduction component including a constituent element to be introduced into the patient's body, such as the injection needle 610, and a remaining component. The introduction component and the remaining component may be detachably coupled to each other. In this case, in the state in which the introduction component is connected to the patient but is separated from the remaining component, the user may couple the remaining component to the downstream side of the connection flow path 300, and may then couple the introduction component and the remaining component to each other. In this case, the liquid passing through the connection flow path 300 may be introduced into the patient's body after sequentially passing through the remaining component and the introduction component. Although not illustrated, a patient connection module according to still another embodiment may include a catheter.

As used in the present disclosure, the terms "upstream" and "downstream" are defined based on the direction in which the medical liquid flows in the connection flow path 300 and the end cap 700 when the pumping module 100 pressurizes the medical liquid. Specifically, directions indicated by arrows F2 and F3 in FIG. 1 are defined as a downstream direction, and a direction opposite the downstream direction is defined as an upstream direction.

The process of injecting the medical liquid into the patient using the medical liquid injection apparatus set 1 according to embodiments of the present disclosure includes a priming step and a medical liquid injection step, which proceed sequentially.

In the state in which the patient connection module 600 or 600' is separated from the patient or in the state in the introduction component of the patient connection module 600 or 600' is connected to the patient but the remaining component is separated, the priming step proceeds. In the priming step, the end cap 700 is connected to the downstream side end of the connection flow path 300, and the priming liquid is caused to flow along the connection flow path 300. The priming liquid flowing along the connection flow path 300 is introduced into the end cap 700, and the air inside the connection flow path 300 is discharged to the outside through the end cap 700. Ac-cordingly, the inside of the connection flow path 300 and the end cap 700 is filled with the priming liquid.

The priming liquid is a liquid that flows along the connection flow path 300 to fill the inside of the connection flow path 300 and is introduced into the end cap 700. The priming liquid may be a medical liquid to be injected into a patient or a saline solution to be used in place of the medical liquid.

The refractive index ($n_a$) of air is 1. The priming liquid has a refractive index ($n_p$) greater than 1. The priming liquid has a refractive index ($n_p$) substantially similar to that of water. The refractive index ($n_p$) is about 1.333.

The end cap 700 is connected to the downstream side of the connection flow path 300 such that the priming liquid is introduced into the end cap 700. The end cap 700 is configured to allow air and the priming liquid to flow therein. The end cap 700 may be configured to allow air to flow out, but to prevent the priming liquid from flowing out.

When the end cap 700 is filled with the priming liquid, the end cap 700 is separated from the connection flow path 300 and the connection flow path 300 may be connected to the patient connection module 600 or 600' or the connection flow path 300 may be connected to the remaining component. Thereafter, in order to discharge the air in the patient connection module 600 or 600', the inside of the patient connection module 600 or 600' may be filled with the priming liquid.

After connecting the patient connection module 600 or 600' to the patient, the medical liquid injection step is performed. In the medical liquid injection step, the medical liquid is introduced into the patient's body in response to the pressurization in the pumping module 100. When the priming liquid is not a medical liquid but is a saline solution or the like, the priming liquid first flows into the patient's body, and the medical liquid flowing after the priming liquid may flow into the patient's body.

Referring to FIG. 1, the pumping module 100 includes a chamber 110 configured to accommodate a medical liquid. The chamber 110 forms an inner space with a pressurizing unit 120. The medical liquid may be stored in the inner space. In another embodiment, a saline solution or the like may be temporarily stored in the inner space. In the chamber 110, a discharge port portion 111 through which the liquid in the chamber 110 is discharged is formed.

The pumping module 100 includes a pressurizing unit 120 configured to pressurize the liquid within the chamber 110. The pressurizing unit 120 may pressurize the liquid in the chamber 110 by moving in a predetermined pressurizing direction Ap1. When the inside of the chamber 110 is being filled with the liquid, the pressurizing unit 120 moves in the direction Ap2 opposite the pressurizing direction Ap1. FIG. 1 illustrates the position of the pressurizing unit 120 in the state in which the pressurizing unit 120 moves in the opposite direction Ap2 with reference to 120A.

The pumping module 100 may include a pressurizing operation portion 130 that provides power to move the pressurizing unit 120 in the pressurizing direction Ap1. As an example, the pressurizing operation portion 130 may be configured to pressurize the liquid in the chamber 110 using a volumetric expansion by gas activation. As another example, the pressurizing operation portion 130 may provide a portion that can be held by the user, and may move the pressurizing unit 120 in the pressurizing direction Ap1 with the force of the user.

Although not illustrated, as another example, the pressurizing unit 120 may be configured to pressurize the liquid using the elastic force of an elastic body such as a balloon. In this case, the pressurizing unit 120 may be configured to pressurize the liquid in the balloon.

The chamber 110 can be filled with the liquid by using the port module 200. The liquid may be introduced into the connection flow path 300 or the chamber 110 through the port module 200 from the outside. The port module 200 is connected to the connection flow path 300, but in another non-illustrated embodiment, the port module 200 may be connected to the chamber 110.

The port module 200 includes a first extension 210 connected to the downstream end of the first connection portion 310 of the connection flow path 300 and a second extension 220 connected to the upstream end of the second connection portion 320 of the connection flow path 300. The port module 200 includes an inlet part 230 configured to allow liquid to be introduced therethrough from the outside and an inlet port opening and closing part 240 configured to be detachably coupled to the inlet part 230. Arrow E1 in FIG. 1 indicates the direction of coupling/decoupling the inlet port opening and closing part 240 with respect to the inlet part 230.

The connection flow path 300 is configured to guide the flow of the priming liquid. The connection flow path 300 may guide the movement of the medical liquid from the pumping module 100 to the end cap 700. The upstream end of the connection flow path 300 is connected to the pumping module 100. The downstream end of the connection flow path 300 is configured to be connectable to the end cap 700. The downstream end of the connection flow path 300 is configured to be connectable to the patient connection module 600 or 600'.

The upstream side of the connection flow path 300 is connected to the pumping module 100. The connection flow path 300 includes an upstream connection part 350 connected to the discharge port portion 111.

The downstream side of the connection flow path 300 may be connected to the end cap 700. The connection flow path 300 includes a downstream connection part 360 connected to the end cap 700. The downstream connection part 360 may be separated from the end cap 700 and may be connected to the patient connection module 600 or 600'.

The connection flow path 300 includes a first connection part 310 that interconnects the upstream connection part 350 and the first extension 210 of the port module 200. The connection flow path 300 includes a second connection part 320 that interconnects the second extension 220 of the port module 200 and a filter module 500. The connection flow path 300 includes a third connection part 330 that interconnects the filter module 500 and the downstream connection part 360.

At least one connection tube opening and closing module 400 may be configured. The connection tube opening and closing module 400 may press the outside of the connection flow path 300 in order to block the flow of the liquid at a point in the connection flow path 300. The connection tube opening and closing module 400 includes a first opening and closing module 410 capable of changing whether or not a point B1 of the first connection part 310 is opened, and a second opening and closing module 420 capable of changing whether or not a point B2 of the second connection part 320 is opened. For example, the connection tube opening and closing module 400 may be configured in a clamp shape.

The filter module 500 may be disposed on the connection flow path 300. The filter module 500 may include a filter casing 510 connected to the connection flow path 300 and a filter 520 disposed in the filter casing 510.

The patient connection module 600 or 600' is configured to be connectable to the downstream connection part 360. The liquid that has passed through the inside of the connection flow path 300 may move to the patient connection module 600 or 600' to flow into the patient's body.

The patient connection module 600 or 600' may include an injection needle 610 configured to be capable of being infiltrated into the skin of the patient. The patient connection module 600 or 600' includes an injection support 620 that supports the injection needle 610.

The patient connection module 600 or 600' includes a module coupling part 630 coupled with the downstream connection part 360 of the connection flow path 300. Arrow C2 in FIG. 1 indicates the direction of coupling/decoupling the module coupling part 630 with respect to the downstream connection part 360.

The patient connection module 600 according to an embodiment may be configured such that the injection needle 610, the injection support part 620, and the module coupling part 630 are sequentially connected. The patient connection module 600' according to another embodiment further includes a patient connection tube fixing part 650' connected to the downstream side of the module coupling part 630. The patient connection module 600' further includes a patient connection tube 640' that interconnects the patient connection fixing part 650' and the injection support part 620. The patient connection tube 640' may be formed of a flexible material. For example, the introduction component may include the injection needle 610 and the injection support part 620, and the remaining component may be configured to be connected to the module coupling part 630, the patient connection tube fixing part 650', and the patient connection tube 640'.

The priming step and the medical liquid injection step according to an embodiment will be described as follows. In the priming step according to the embodiment, a saline solution, which is not a medical liquid, is used as the priming liquid. In the priming step according to the embodiment, the end cap 700 is connected to the downstream connection part 360 of the connection flow path 300, the inlet port opening and closing part 240 is separated from the inlet part 230, the first connection part 310 is blocked by the first opening and closing module 410 (see B1), and the remaining portion, other than the first connection part 310, of the connection flow path 300 is opened. Referring to arrows F1 and F3, the priming liquid such as a saline solution flows sequentially through the inlet part 230, the second extension 220, the second connection part 320, the third connection part 330, and the end cap 700, whereby the inside of the connection flow path 300 and the end cap 700 are filled with the priming liquid.

After the priming step according to the embodiment, the medical liquid injection step according to the embodiment proceeds. In the medical liquid injection step according to the embodiment, the patient connection module 600 or 600' is connected to the downstream connection part 360 of the connection flow path 300 instead of the end cap 700, the inlet port opening and closing part 240 is separated from the inlet part 230, the second connection part 320 is blocked by the second connection tube opening and closing module 420, and the first connection tube opening and closing module 410 is separated from the first connection part 310 so as to open the first connection part 310. Referring to arrow F0, as the medical liquid flows into the chamber 110 through the port module 200 and the first connection part 310, the pressurizing unit 120 moves in the above-mentioned direction Ap2. Thereafter, the inlet port opening and closing part 240 is coupled to the inlet part 230, and the second connection tube opening and closing module 420 is separated from the second connection part 320 so as to open the connection flow path 300. Referring to arrows F2 and F3, thereafter, by moving the pressurizing unit 120 in the pressurizing direction Ap1, the medical liquid is able to sequentially pass through the connection flow path 300 and the patient connection module 600 or 600'.

The priming step and the medical liquid injection step according to another embodiment will be described as follows. In the priming step according to another embodiment, a saline solution, which is not a medical liquid, is used as the priming liquid. In the another embodiment, the inside of the chamber 110 is filled with a medical liquid, the end cap 700 is connected to the downstream connection part 360 of the connection flow path 300, the inlet part 230 is blocked by the inlet port opening and closing part 240, and the connection tube opening and closing module 400 is separated from the connection channel 300 so as to open the connection flow path 300. Referring to arrows F2 and F3, thereafter, by moving the pressurizing unit 120 in the pressurizing direction Ap1 so that the medical liquid serving as the priming liquid sequentially flows through the connection flow path 300 and the end cap 700, the inside of the flow path 300 and the end cap 700 is filled with the priming liquid.

After the priming step according to another embodiment, the medical liquid injection step according to another embodiment proceeds. In the medical liquid injection step according to another embodiment, the patient connection module 600 or 600' is connected to the downstream connection part 360 of the connection flow path 300, instead of the end cap 700. Referring to arrows F2 and F3, thereafter, by further moving the pressurizing unit 120 in the pressurizing direction API, the medical liquid is able to sequentially pass through the connection flow path 300 and the patient connection module 600 or 600'.

Figure 2:
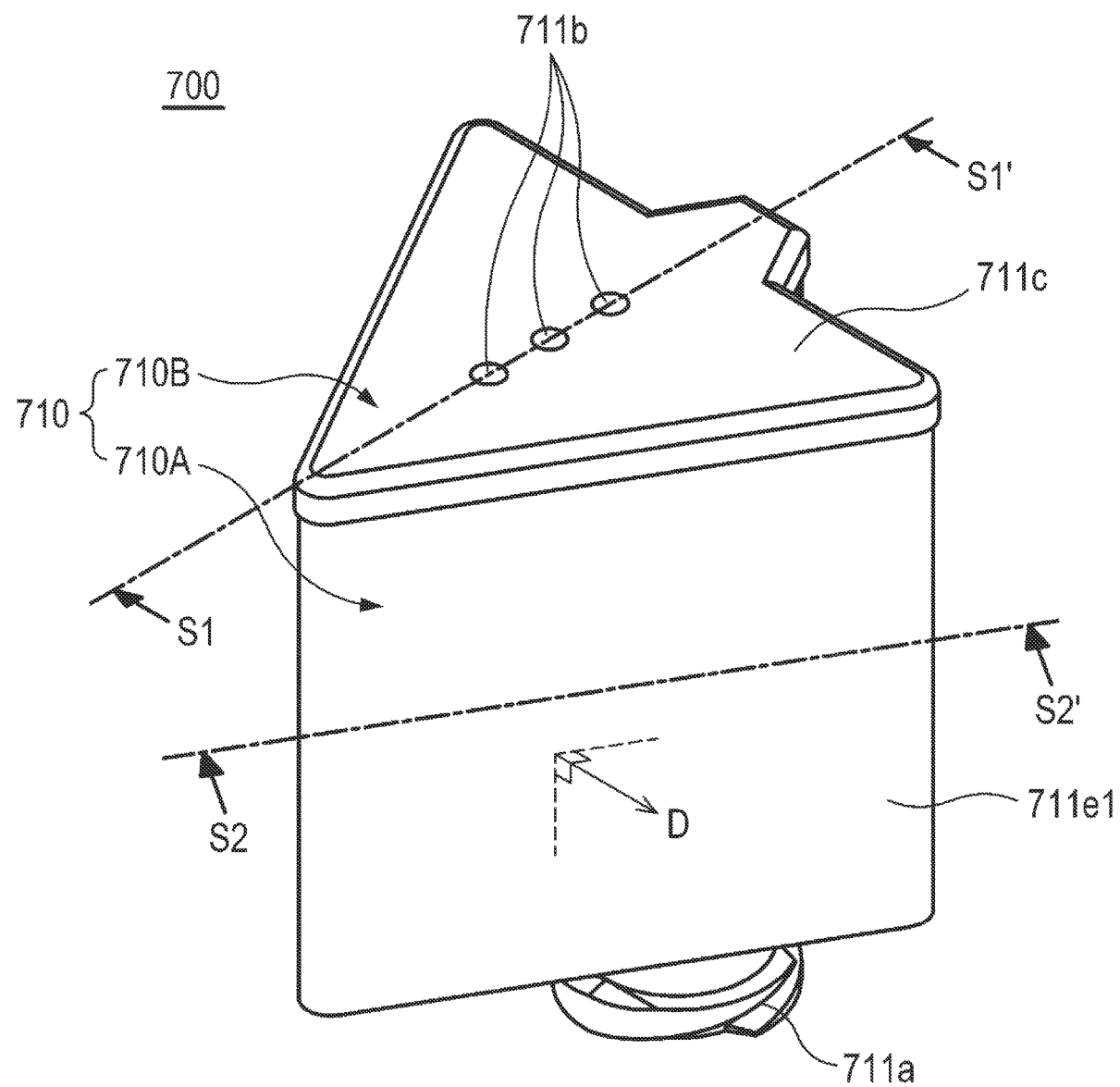
FIG. 2 is a perspective view illustrating an end cap 700 according to the embodiment of FIG. 1.

FIG. 2 is a perspective view illustrating an end cap 700 according to the embodiment of FIG. 1. Referring to FIG. 2, the end cap 700 for a medical liquid injection apparatus will be described as follows.

The end cap 700 includes a body part 710 connected to the connection flow path 300. The body part 710 may form an external appearance. The body part 710 may have a triangular prism shape as a whole. The body part 710 may include a housing member 710A and a cap member 710B, which are coupled to each other. The housing member 710A is located on the upstream side and the cap member 710B is located on the downstream side.

The priming liquid may be introduced into the end cap 700 through an inlet port 711b of the housing member 710A. The housing member 710A may include a first side surface portion 711e1 faces a display direction D to be described later.

The air inside the end cap 700 may flow out of the end cap 700 through an outlet port 711b of the cap member 710B. The cap member 710B may include a downstream side surface 711c faces the downstream direction.

Figure 3:
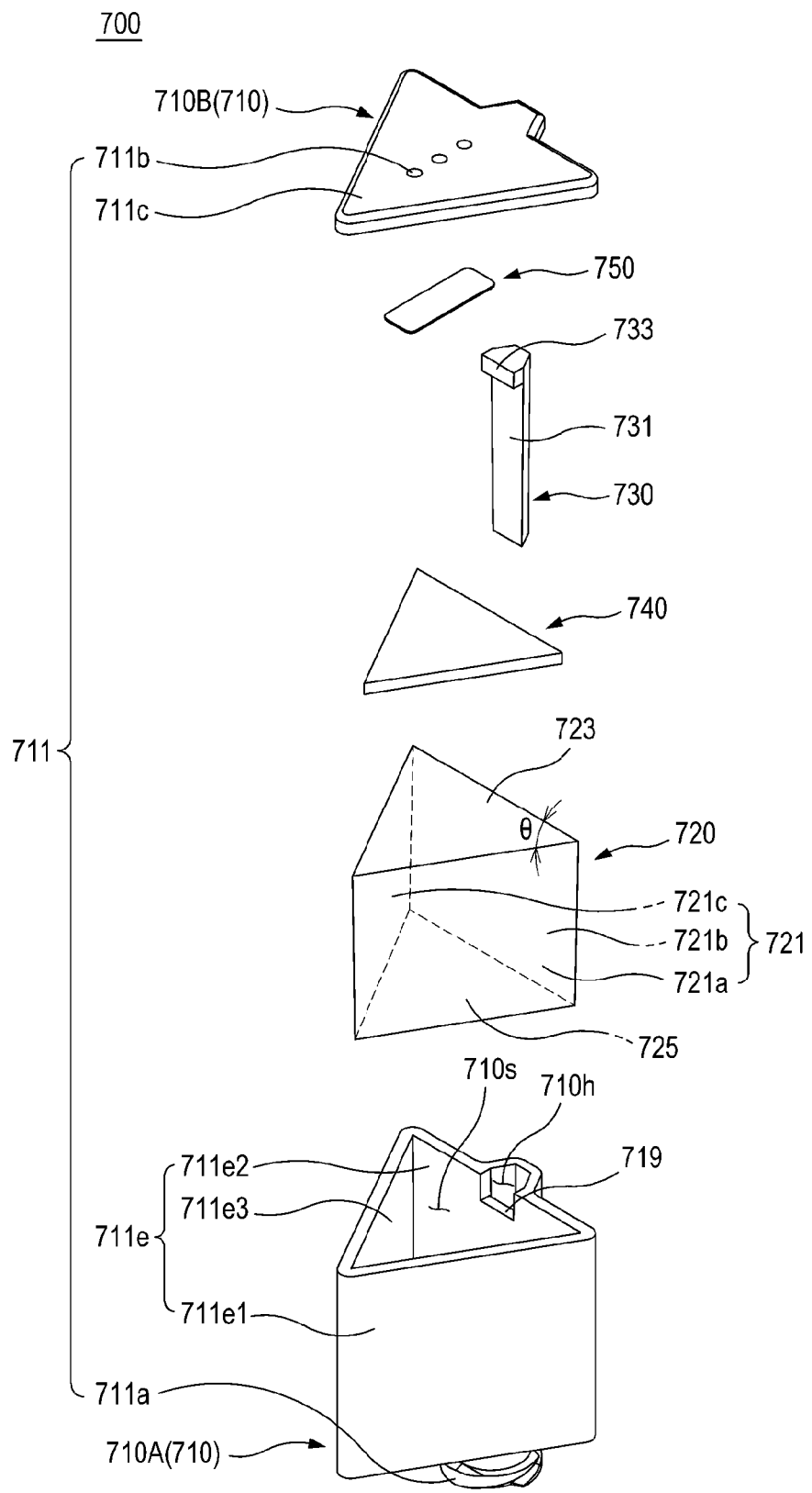
FIGS. 3 and 4 are exploded perspective views illustrating the end cap 700 of FIG. 2, which is viewed in different directions.
Figure 4:
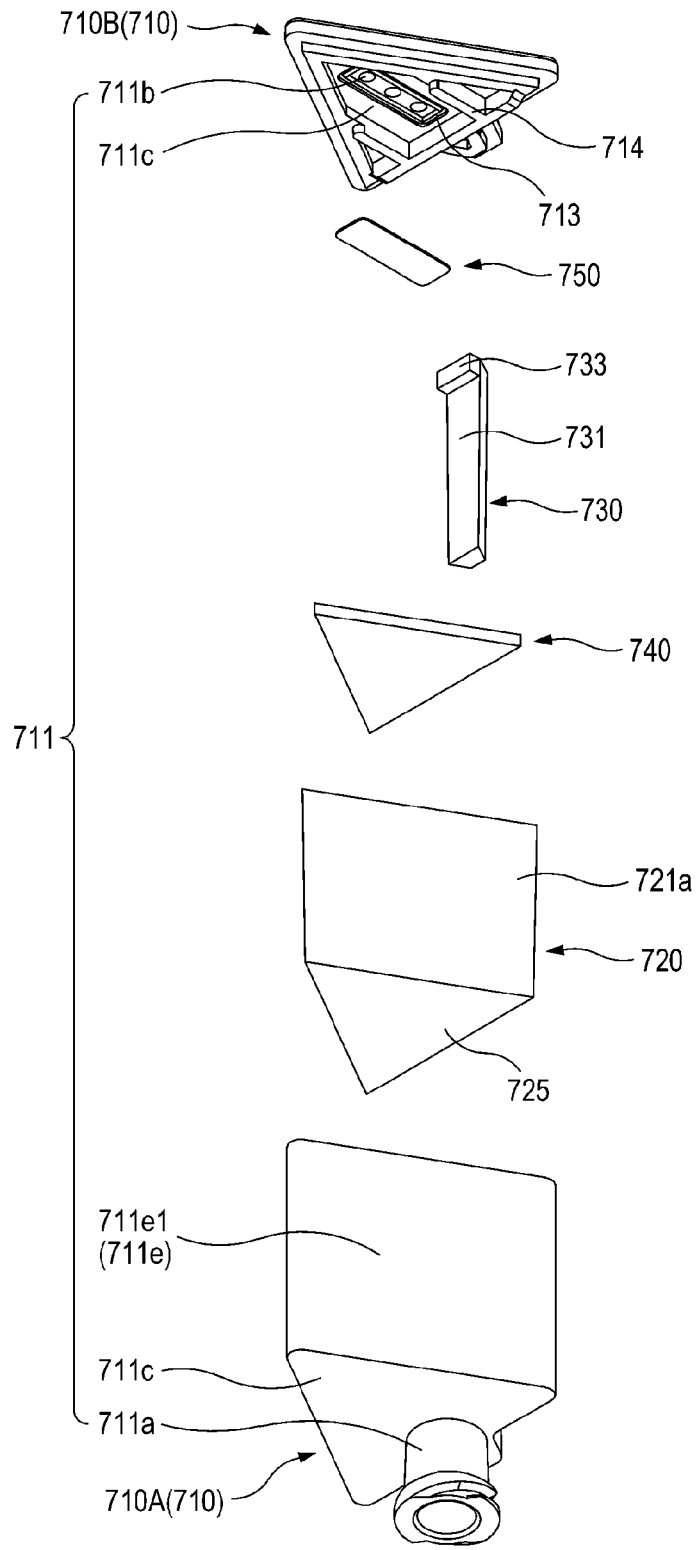

FIGS. 3 and 4 are exploded perspective views illustrating the end cap 700 of FIG. 2, which is viewed in different directions. The configuration of the end cap 700 will be described in detail with reference to FIGS. 3 and 4. The end cap 700 may include a body part 710, a refraction part 720, a display member 730, a liquid absorption part 740, and a filter part 750.

The body part 710 includes a casing part 711 that forms an external appearance. In this embodiment, the casing part 711 constitutes a part of the cap member 710B and a part of the housing member 710A, but the method of configuring the casing part 711 needs not be limited.

The casing part 711 includes an inlet port 711a configured to allow the priming liquid to be introduced therethrough from the connection flow path 300. The inlet port 711a forms a hole that is connected to the inner space. The inlet port 711a may be formed to protrude toward the upstream side from the upstream side surface 711c of the casing part 711. The inlet port 711a may form a screw-like protrusion to be coupled with the downstream end of the connection flow path 300.

The casing part 711 includes an outlet port 711b configured to allow air to flow out therethrough from the inside of the end cap 700. The outlet port 711b may be formed in the downstream side surface 711d of the casing part 711. The outlet port 711b may form a plurality of holes through the downstream side surface 711d of the casing part 711.

The outer surface of the casing part 711 includes the upstream side surface 711c, the downstream side surface 711d, and a peripheral side surface 711e. The upstream side surface 711c faces the upstream direction, and the downstream side surface 711d faces the downstream direction. The peripheral side surface 711e is a surface that surrounds the periphery around the upstream-downstream direction. The peripheral side surface 711e is arranged to interconnect the upstream side surface 711c and the downstream side surface 711d.

The peripheral side surface 711e may include a first side surface portion 711e1 corresponding to the first surface 721a of the refraction part 720. The inner surface of the first side surface portion 711e1 faces the first surface 721a. The inner surface of the first side surface portion 711e1 may be in contact with the first surface 721a.

The peripheral side surface 711e may include a second side surface portion 711e2 corresponding to the second surface 721b of the refraction part 720. The inner surface of the second side surface portion 711e2 faces the second surface 721b. At least a part of the inner surface of the second side surface portion 711e2 is spaced apart from the second surface 721b.

The peripheral side surface 711e may include a third side surface portion 711e3 corresponding to the third surface 721c of the refraction part 720. The inner surface of the third side surface portion 711e3 faces the third surface 721c. The inner surface of the third side surface portion 711e3 may be in contact with the third surface 721c.

The body part 710 forms an arrangement space 710s in which the refraction part 720 is located. The arrangement space 710s formed in the housing member 710A may be formed to be recessed toward the upstream side. The cap member 710B may cover the downstream side of the arrangement space 710s in the state in which the refraction part 720 is disposed in the arrangement space 710s.

The body part 710 may form an insertion hole 710h in which the indication part 731 is located. The insertion hole 710h formed in the housing member 710A may be formed to be recessed toward the upstream side. The cap member 710B may cover the downstream side of the insertion hole 710h in the state in which the indication part 731 is disposed in the insertion hole 710h.

The body part 710 may include a filter seat part 713 on which the filter part 750 is seated. The filter seat part 713 may be located on the inner surface of the downstream side surface 711d. A hole of the outflow port 711b is formed in the filter seat part 713. The filter seat part 713 may include a rib that guides the peripheral position of the filter part 750.

The body part 710 may include a spacing part 714 that spaces the liquid absorption part 740 apart from the filter part 750. The spacing part 714 may be formed to protrude in the upstream direction from the inner surface of the downstream side surface 711d. The spacing part 714 may be formed in a rib shape. The upstream end of the spacing part 714 may come into contact with the liquid absorption part 740 to limit the movement of the liquid absorption part 740 in the downstream direction.

The body part 710 may further include an auxiliary refraction part 719. The auxiliary refraction part 719 may be integrally formed with the housing member A1. The auxiliary refraction part 719 is disposed between the arrangement space 710s and the insertion hole 710h. The auxiliary refraction part 719 is disposed between the refraction part 720 and the indication part 731. The auxiliary refraction part 719 is formed of a transparent material that transmits light. The end cap 700 according to the present embodiment includes the auxiliary refraction part 719, but it is possible to implement embodiments that do not include the auxiliary refraction part 719 as described below.

The refraction part 720 is formed of a transparent material having a refractive index ($n_r$) larger than 1. The refraction part 720 may be formed of a transparent material having a refractive index $n_r$ greater than the refractive index $n_p$ of the priming liquid (see FIG. 9B), but may be formed of a transparent material having a refractive index $n_r$ of not greater than the refractive index $n_p$ (See FIG. 9C).

The refraction part 720 may be formed in a triangular prism shape as a whole. For example, the refraction part 720 may be a prism.

The refraction part 720 is disposed in the casing part 711. The refraction part 720 may be disposed inside the casing part 711. The refraction part 720 may face the inlet port 711a in the upstream direction. The refraction part 720 may face the outlet port 711b in the downstream direction.

The outer surface of the refraction part 720 includes an upstream surface 725, a downstream surface 723, and a peripheral surface 721. The upstream surface 725 faces the upstream direction, and the downstream surface 723 faces the downstream direction. The peripheral surface 721 is a surface that surrounds the periphery around the upstream-downstream direction. The peripheral surface 721 is disposed so as to interconnect the upstream surface 725 and the downstream surface 723.

The peripheral surface 721 includes a first surface 721a and a second surface 721b which form an internal angle θ, which is smaller than 90 degrees. Each of the first surface 721a and the second surface 721b forms a plane.

The peripheral surface 721 may further include a third surface 721c that faces a direction different from the directions that the first surface 721a and the second surface 721b face. The third surface 721c may be a surface other than the first surface 721a and the second surface 721b in the peripheral surface 721. The third surface 721c may form a plane. The peripheral surface 721 may only include the first surface 721a, the second surface 721b, and the third surface, but the peripheral surface 721 may include more than three surfaces and may include a curved surface.

In this embodiment, the refraction part 720 is made of acrylonitrile butadiene styrene (ABS) resin. In this embodiment, the refractive index $n_r$ of the refraction part 720 is about 1.518. When the refractive index $n_r$ of the refraction part 720 is 1.518 and the refractive index $n_p$ of the priming liquid is 1.333, the internal angle θ may be 41.2 degrees or more and smaller than 61.4 degrees.

In this embodiment, the interior angle θ is about 60 degrees. The refractive index $n_r$ of the refraction part 720 may be 1.155 or more and smaller than 1.539 when the internal angle θ is 60 degrees and the refractive index $n_p$ of the priming liquid is 1.333.

The display member 730 may be coupled with the body part 710. The display member 730 is disposed inside the casing part 711. The display member 730 may be formed to be elongated in the upstream-downstream direction as a whole.

The display member 730 includes an indication part 731 facing and spaced apart from the second surface 721b. The indication part 731 may be configured to be opaque. The indication part 731 may have a color different from the surrounding color thereof. In this embodiment, the indication part 731 may be formed as a part of the display member 730, which is a separate member. However, in another embodiment (not illustrated), for example, an indication part colored in an inner surface facing the second surface 721b of the body part 710 may be used in place of the indication part 731.

The display member 730 may include an engagement portion 733, which is engaged with the body part 710. The engagement portion 733 may be disposed at the downstream end of the indication part 731. The engagement portion 733 may be in contact with the downstream end of the auxiliary refraction part 719 to be engaged with the downstream end of the auxiliary refraction part 719. The engagement portion 733 may be formed to protrude inward from the indication part 731.

The liquid absorption part 740 is configured to absorb the priming liquid. The liquid absorption part 740 assists the passage of air while absorbing the priming liquid. The liquid absorption part 740 may be in the form of a sponge. The liquid absorption part 740 may be disposed on the downstream side of the refraction part 720. The liquid absorption part 740 may be disposed on the upstream side of the filter part 750. Since the liquid absorption part 740 absorbs the priming liquid, it is possible to prevent the priming liquid from forming a liquid film and disturbing air discharge by coming into contact the filter part 750.

A hydrophobic filter part 750 configured to pass air therethrough may be provided. The filter part 750 prevents the passage of the priming liquid. The filter part 750 is disposed on the downstream side of the liquid absorption part 740. The filter part 750 may be fixed to the inner surface of the casing part 711. Specifically, the filter part 750 may be fixed to the filter seat part 713 via ultrasonic bonding or other bonding methods.

The end cap 700 may further include a check valve (not illustrated) to prevent backflow. The check valve serves to prevent the priming liquid introduced into the end cap 700 from flowing out through the inlet port 711a. The check valve may be disposed inside the inlet port 711a.

Figure 5:
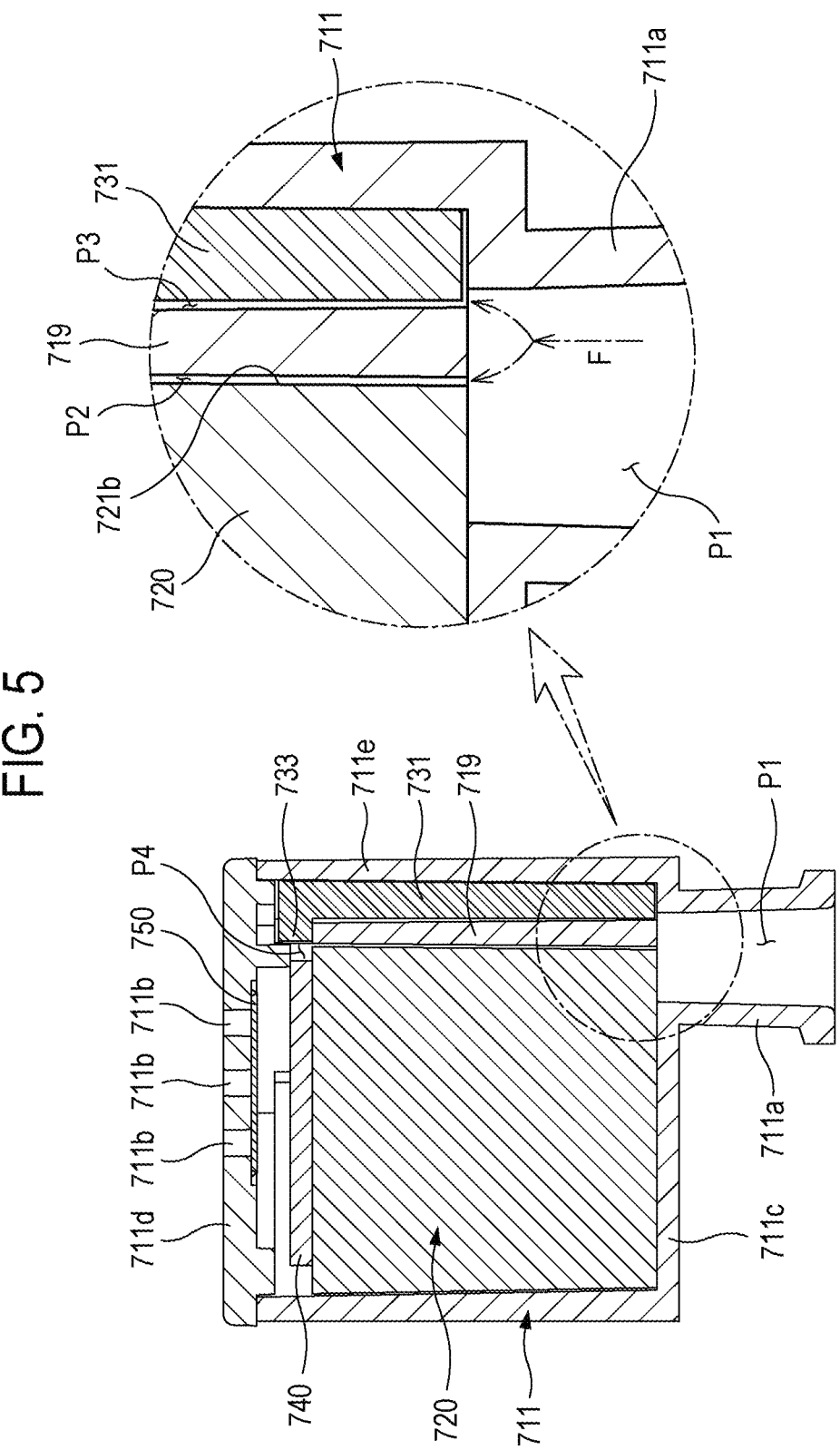
FIG. 5 illustrates a vertical cross-sectional view of the end cap 700 taken along line S1-S1' in FIG. 2 and a partially enlarged view of the end cap 700.

FIG. 5 illustrates a vertical cross-sectional view of the end cap 700 taken along line S1-S1' in FIG. 2 and a partially enlarged view of the end cap 700. Next, an inner feature and a passage in the end cap 700 will be described with reference to FIG. 5.

The end cap 700 has therein a passage in which the priming liquid to be introduced is movable. The inlet port 711a is configured to allow the priming liquid to flow into the passage therethrough. The outflow port 711b is configured to allow air to flow out from the inside of the passage therethrough.

The indication part 731 is disposed to be spaced apart from the second surface 721b of the refraction part 720. A part of the passage is located between the second surface 721b and the indication part 731. The passage is configured to be connected from the inlet port 711a to the space between the second surface 721b and the indication part 731. The passage is configured to be connected from the space between the second surface 721b and the indication part 731 to the liquid absorption part 740.

The passage includes a main passage portion P2 located between the second surface 721b and the indication part 731. In FIG. 5, the main passage portion P2 may be a gap between the second surface 721b and the auxiliary refraction part 719, but in the embodiment in which the auxiliary refraction part 719 is not provided, the main passage portion P2 may be a gap between the second surface 721b and the indication part 731. The priming liquid is movable from the upstream side to the downstream side of the refraction part 720 along the main passage portion P2.

The passage includes an upstream passage portion P1 configured to guide the priming liquid introduced through the inlet port 711a to the main passage portion P2 (see arrow F in FIG. 5). The passage includes a downstream passage portion P4 configured to guide the priming liquid, which passes through the main passage portion P2, to the liquid absorption part 740.

The passage may further include an auxiliary passage portion P3 located between the second surface 721b and the indication part 731 and configured separately from the main passage portion P2. The auxiliary passage portion P3 may be a gap between the auxiliary refraction part 719 and the indication part 731. The priming liquid may flow separately into the main passage portion P2 and the auxiliary passage portion P3 through the upstream passage portion P1. In FIG. 5, the auxiliary passage portion P3 is configured. However, in another embodiment in which the auxiliary refraction part 719 and the indication part 731 are in contact with each other or in still another embodiment in which the auxiliary refraction part 719 is not provided, the auxiliary passage portion P3 may not be configured.

The liquid absorption part 740 is disposed on the downstream side of the part of the passage located between the second surface 721b and the indication part 731 (the main passage portion P2). The liquid absorption part 740 may be interposed between the refraction part 720 and the spacing part 714.

FIG. 6 illustrates a horizontal cross-sectional view of the end cap 700 of FIG. 2, taken along line S2-S2' and partially enlarged views taken according to a first cm-bodiment (E1), a second embodiment (E2), and a third embodiment (E3). Referring to FIG. 6, the outward direction perpendicular to the first surface 721a is defined as "display direction D", and the direction opposite the display direction D is defined as "observation direction V". The direction of the first surface 712a when the first surface 721a and the second surface 721b form the internal angle θ in the state of being viewed in the observation direction V is defined as the rightward direction R, and the direction opposite the rightward direction R is defined as "leftward direction L".

In the first embodiment E1, the end cap 700 includes the auxiliary refraction part 719, and forms the main passage portion P2 and the auxiliary passage portion P3. The auxiliary refraction part 719 is disposed between the second surface 721b and the indication part 731, the second surface 721b and the auxiliary refraction part 719 are spaced apart from each other, and the auxiliary refraction part 719 and the indication part 731 are spaced apart from each other.

In the second embodiment E2, the end cap 700 includes the auxiliary refraction part 719, and forms the main passage portion P2 but does not form the auxiliary passage portion P3. The auxiliary refraction part 719 is disposed between the second surface 721b and the indication part 731, the second surface 721b and the auxiliary refraction part 719 are spaced apart from each other, and the auxiliary refraction part 719 and the indication part 731 are in contact with each other.

In the third embodiment E3, the end cap 700 does not include the auxiliary refraction part 719, and forms the main passage portion P2 but does not form the auxiliary passage portion P3. The main passage portion P2 is disposed between the second surface 721b and the indication part 731.

The surfaces 711e1 and 711e3, other than the second surface 721b, in the peripheral surface 721 of the refraction part 720 including the first surface 721a and the second surface 721b, are in contact with the inner surface of the casing part 711. The first surface 721a may come in contact with the first side surface portion 711e1 of the casing part 711. The third surface 721c may come in contact with the third side surface portion 711e3 of the casing part 711. The second surface 721b is spaced apart from the second side surface portion 711e2 of the casing part 711, and in the embodiment including the auxiliary refraction part 719. The second surface 721b is spaced apart from the second side surface portion 711e2 and the auxiliary refraction part 719. This allows the priming liquid to intensively flow in the space between the indication part 731 and the second surface.

FIGS. 7A and 7B are elevation views of the end cap 700 of FIG. 6 viewed from the observation direction V, in which FIG. 7A is a view illustrating a first state before a priming liquid is introduced into the end cap 700 and FIG. 7B is a view illustrating a second state after the cap 700 is filled with the priming liquid. In the first state, the passage is filled with air. In the second state, the passage is filled with the priming liquid.

Referring to FIG. 7A, the refraction part 720 is configured such that all light beams that start from the indication part 731 in the first state move in directions different from the display direction D. That is, in the first state, all the light beams that start from the indication part 731 do not move in the display direction D. As a result, the image of the indication part 731 is not seen through a transparent portion T when viewed in the observation direction V. In the first state, an image totally reflected on the second surface 721b is capable of being seen in the transparent portion T when viewed in the observation direction V.

Referring to FIG. 7B, the refraction part 720 is configured such that some of the light beams that start from the indication part 731 in the second state move in the display direction D. That is, among the light beams that start from the indication part 731, the light beams that start at a predetermined angle are refracted from the second surface 721b and moved in the display direction D. As a result, the image of the indication part 731 is seen through the transparent portion T when viewed in the observation direction V.

FIG. 8 is a cross-sectional view illustrating FIG. 6 without hatching, showing a transparent portion T and a blind portion B. Arrows L0, L1, L2, and L3 indicate light traveling directions, and an indication "X" on an arrow means that light movement is interfered by the blind portion B.

Referring to FIG. 8, the transparent portion T is formed so as to transmit a light beam L0 moving in the display direction D to the outside. Specifically, a specific area 721T of the first surface 721a corresponding to the transparent portion T may be smoothly formed, and a partial area of the peripheral side surface 711e corresponding to the transparent portion T may be formed transparently. The light beam L0 is transmitted through the transparent portion T, and an image produced by the light beam L0 is capable of being observed in the observation direction V.

Areas 721aB, 721bB, and 721cB, other than the area 721T corresponding to the transparent portion T, in the peripheral surface 721 including the first surface 721a and the second surface 721b are formed with the blind portion B, which interferes with light passing through the refraction part 720 to the outside. Here, the description "the blind portion B interferes with light" may mean that the blind portion blocks light, scatters light, or transmits light with transparency lower than that of the transparent portion T.

For example, the blind portion B may include a separate member such as tape attached to the casing part 711 or the refraction part 720. The separate member may be formed of an opaque material or a material having transparency lower than that of the transparent portion T.

For example, the blind portion B may include a separate painted surface formed on the casing part 711 or the refraction part 720 through painting. The separate painted surface may be formed of an opaque material or a material having transparency lower than that of the transparent portion T.

As another example, the blind portion B may be formed by corroding the surface of the casing part 711 or the surface of the refraction part 720. As another example, the blind part B may include a part of the casing part 711 formed of an opaque material or a material having a lower transparency than that of the transparent portion T.

As described above, the blind part B may be configured through various methods or a combination thereof. However, it is preferable that the blind portion B corresponding to the second surface 721b be disposed in the casing part 711 and the second surface 721b is configured to transmit light.

The transparent portion T is configured to correspond to the specific area 721T of the first surface 721a. The blind portion B is configured to correspond to shield areas 721aB, 721bB, and 721cB, other than the specific area 721T, in the peripheral side surface 711e of the refraction part 720. The shield areas 721aB, 721bB, and 721cB may include a shield area 721aB located on the first surface 721a and a shield area 721bB located on the second surface 721b. The shield areas 721aB, 721bB, and 721cB may further include a shield area 721cB located on the third surface 721c. The blind portion B interferes with a light beam L1 to move to the outside through the shield area 721aB, interferes with a light beam L2 to move to the outside through the shield area 721bB, and interferes with a light beam L3 to move to the outside through the shield area 721cB.

The specific area 721T may be configured to be located only on the first surface 721a of the peripheral surface 721. In this case, the entire second surface 721b becomes the shield area 721bB, and the entire third surface 721c becomes the shield area 721cB.

The specific area 721T may be located in the direction of the internal angle θ that the first surface 721a forms with the second surface 721b with respect to the area 721aB other than the specific area 721T of the first surface 721a. That is, the specific area 721T may be located in the rightward direction R of the shield area 721aB. This makes it possible to block the area, in which the image of the indication part 731 is visible when viewed in a direction between the observation direction V and the rightward direction R in the first state, by the blind portion B corresponding to the shield area 721aB. It is also possible to block the area in which the image of the indication part 731 is reflected on the third surface 721c to be visible by the blind portion B corresponding to the shield area 721aB.

The boundary between the specific area 721T and the shield area 721aB may be formed parallel to the height direction of the refraction part 720. Here, the "height direction" of the refraction part 720 means a direction perpendicular to the display direction D, the observation direction V, the rightward direction R, and the leftward direction L. The boundary between the specific area 721T and the shield area 721aB may be located in the rightward direction R with respect to the center of the first surface 721a. The area of the specific area 721T may be smaller than the area of the shield area 721aB. The first surface 721a may be divided into left and right portions at a ratio of approximately 2:1 with reference to the boundary between the specific area 721T and the shield area 721aB.

FIGS. 9A to 9C are conceptual cross-sectional views formed by horizontally cutting a refraction part 720 and an indication part 731 in an embodiment in which an auxiliary refraction part 719 is not provided, in which FIG. 9A illustrates exemplary light traveling paths in the state in which a main passage portion P2 is filled with air and FIGS. 9B and 9C illustrates exemplary light traveling paths in the state in which the main passage portion P2 is filled with the priming liquid. In FIGS. 9A to 9C, LR, LF, and LD indicate paths of light beams, and refraction on the first surface 721a is omitted in the illustration of paths of light beams LR and LF.

The refractive index $n_r$ of the refraction part 720 is greater than 1, which is the refractive index $n_a$ of air. The refractive index $(n_p)$ of the priming liquid is also greater than 1. FIG. 9B illustrates a path of light when the refractive index $n_r$ is greater than the refractive index $n_p$, and FIG. 9C illustrates a path of light when the refractive index $n_r$ is smaller than the refractive index $n_p$.

Referring to FIG. 9A, in the first state, the main passage portion P2 is filled with air having the refractive index $n_a$. The refraction part 720 is configured to move a light beam LD totally reflected from the second surface 721b in the display direction D in the first state. A critical angle A1 of a light beam incident on the inner surface of the second surface 721b in the first state may be obtained through Equation 1 as follows.

$$\sin A1 = \frac{n_a}{n_r} = \frac{1}{n_r} \qquad \text{Equation 1}$$

-continued $$A1 = \sin^{-1}\left(\frac{1}{n_r}\right)$$

A light beam LR refracted on the second surface 721b at an angle $A_o$ is smaller than A1 with respect to an imaginary normal line z perpendicular to the second surface 721b travels. Specifically, the light beam LR is incident on the second surface 721b at an incident angle $A_i$ and refracted at a refraction angle $A_o$. In contrast, when viewed at an angle of A1 or more with respect to the normal line z, it is impossible to see the light beam refracted at the second surface 721b. The light beam LF totally reflected on the inner surface of the second surface 721b moves at an angle FA exceeding A1 with respect to the normal line z. Specifically, the light beam LD totally reflected from the inner surface of the second surface 721b at a reflection angle θ travels in the display direction D.

Here, the angle formed by the normal line z and the display direction D is equal to the internal angle θ formed by the first surface 721a and the second surface 721b. Accordingly, in the first state, the internal angle θ is equal to or greater than $$\sin^{-1}\left(\frac{1}{n_r}\right)$$

such that the light beam LD totally reflected from the second surface 721b travels in the display direction D. Here, when this is converted into an expression defining the refractive index $n_r$, the refractive index $n_r$ is equal to or greater than $$\frac{1}{\sin\theta}.$$

Referring to FIG. 9B, in the second state, the main passage portion P2 is filled with air having the refractive index $n_p$. In the embodiment in which the refractive index $n_r$ of FIG. 9B is greater than the refractive index $n_p$, the refraction part 720 is configured such that that a part LD of the light SP that starts from the indication part 731 in the second state is refracted on the second surface 721b so as to travel in the display direction D. It is possible to obtain the critical angle A2 of a light beam incident on the inner surface of the second surface 721b in the second state by the following Equation 2.

$$\sin A2 = \frac{n_p}{n_r} \qquad \text{Equation 2}$$

$$A2 = \sin^{-1}\left(\frac{n_p}{n_r}\right)$$

When $n_p = 1.333$, $A2 = \sin^{-1}\left(\frac{1.333}{n_r}\right)$

The light beam LD refracted on the second surface 721b at an angle $A_o$, is smaller than A2 with respect to an imaginary normal line z perpendicular to the second surface 721b travels. Specifically, the light beam LD is incident on the second surface 721b at an incident angle A; and refracted at a refraction angle $A_o$. The light beam LD traveling in the display direction D is the light refracted at the refraction angle θ on the second surface 721b. In contrast, when viewed at an angle of A2 or more with respect to the normal line z, it is impossible to see the light beam refracted at the second surface 721b. The light beam LF totally reflected on the inner surface of the second surface 721b moves at an angle FA exceeding A2 with respect to the normal line z.

Specifically, the light beam LF totally reflected from the inner surface of the second surface 721b at a reflection angle θ travels in a direction between the display direction D and the rightward direction R.

Here, the angle formed by the normal line z and the display direction D is equal to the internal angle θ formed by the first surface 721a and the second surface 721b. Accordingly, in the second state, the internal angle θ is smaller than $$\sin^{-1}\left(\frac{n_p}{N_r}\right)$$

that the light beam LD refracted on the second surface 721b travels in the display direction D. When the refractive index $n_p$ is 1.333, the internal angle θ is smaller than $$\sin^{-1}\left(\frac{1.333}{n_r}\right).$$

Here, when this is converted into an expression defining the refractive index $n_r$, the refractive index $n_r$ is smaller than $$\frac{n_p}{\sin\theta}.$$

When the refractive index $n_p$ is 1.333, the refractive index $n_r$ is smaller than $$\frac{1.333}{\sin\theta}.$$

Referring to FIG. 9C, in the embodiment in which the refractive index $n_r$ is smaller than the refractive index $n_p$, the refraction part 720 is configured such that that a part LD of the light SP that starts from the indication part in the second state is refracted on the second surface 721b so as to travel in the display direction D. However, in the embodiment of FIG. 9C, it is not necessary to obtain the critical angle of a light beam incident on the inner surface of the second surface 721b, unlike the embodiment of FIG. 9B. This is because the light beam incident on the inner surface of the second surface 721b is not totally reflected since the priming liquid is a medium that is denser than the refraction part 720 (a medium having a refractive index greater than that of the refraction part 720).

The light beam LD refracted on the second surface 721b at an angle θ with respect to an imaginary normal line z perpendicular to the second surface 721b travels. Specifically, the light beam LD is incident on the second surface 721b at an incident angle $A_i$ and refracted at a refraction angle $A_o$. The light beam LD traveling in the display direction D is the light refracted at the refraction angle θ on the second surface 721b.

Here, the angle formed by the normal line z and the display direction D is equal to the internal angle θ formed by the first surface 721a and the second surface 721b. In the embodiment of FIG. 9C, in the second state, it is sufficient if the internal angle θ is smaller than 90 degrees such that the light beam LD refracted on the second surface 721b travels in the display direction D. The present embodiment is applied in the case in which the refractive index $n_r$ is equal to or smaller than the refractive index $n_p$. When the refractive index $n_p$ is 1.333, the refractive index $n_r$ is equal to or smaller than 1.333.

With reference to FIGS. 9A to 9C, the foregoing description is summarized as follows. The internal angle θ is equal to or greater than $$\sin^{-1}\left(\frac{1}{n_r}\right).$$

When refractive index $n_r$ is greater than the refractive index $n_p$, the internal angle θ is equal to or greater than $$\sin^{-1}\left(\frac{1}{n_r}\right)$$

and smaller than $$\sin^{-1}\left(\frac{n_p}{n_r}\right),$$

and when the refractive index $n_r$ is equal to or smaller than the refractive index $n_p$, the internal angle θ is equal to or greater than $$\sin^{-1}\left(\frac{1}{n_r}\right)$$

and smaller than 90 degrees.

In addition, the refractive index $n_r$ is equal to or greater than $$\frac{1}{\sin\theta}.$$

When the refractive index $n_r$ is greater than the refractive index $n_p$, the refractive index $n_r$ is equal to or greater than $$\frac{1}{\sin\theta}$$

and smaller than $$\frac{n_p}{\sin\theta},$$

and when the refractive index $n_r$ is equal to or smaller than the refractive index $n_p$, the refractive index $n_r$ is equal to or greater than $$\frac{1}{\sin\theta}$$

and equal to or smaller than $n_p$. Since $n_p$ is smaller than $$\frac{n_p}{\sin\theta},$$

when combining the two embodiments, the refractive index $n_r$ is equal to or greater than $$\frac{1}{\sin\theta}$$

and smaller than $$\frac{n_p}{\sin\theta}.$$

FIG. 10 is a conceptual cross-sectional view taken by horizontally cutting a refraction part 720, an auxiliary refraction part 719, and an indication part 731 in an embodiment in which the auxiliary refraction part 719 is provided, in which an exemplary light traveling path is illustrated. The refractive index $n_x$ of the medium of the main passage portion P2 and the auxiliary passage portion P3 is the refractive index $n_x$ in the first state and is the refractive index $n_p$ in the second state.

The auxiliary refraction part 719 is formed of a transparent material having a refractive $n_r'$ larger than 1. The auxiliary refraction part 719 is located between the second surface 721b and the indication part 731. The auxiliary refraction part 719 is disposed to be spaced apart from the second surface. The auxiliary refraction part 719 may be disposed to be in contact with the indication part 731. However, the following description will be made with reference to the case in which the auxiliary refraction part 719 is disposed to be spaced apart from the indication part 731.

A part of the passage is located between the second surface 721b and the auxiliary refraction part 719. Specifically, the main passage portion P2 is located between the second surface 721b and the auxiliary refraction part 719. The auxiliary passage portion P3 is located between the auxiliary refraction part 719 and the indication part 731.

In the embodiment in which the auxiliary refraction part 719 is provided, the second surface 721b also forms a boundary with the main passage portion P2. Thus, the ranges of the internal angle θ and the refractive index $n_r$ are as described above with reference to FIGS. 9A to 9C. In the embodiment in which the auxiliary refraction part 719 is provided, there is a difference in the light traveling path, and the following description will focus on the difference.

Referring to FIG. 10, a part (LR) of the light SP that starts from the indication part 731 is incident on the boundary between the auxiliary passage portion P3 and the auxiliary refraction part 719 at an incident angle Aa and is refracted at a refraction angle Ab. The light beam LR traveling inside the auxiliary refraction part 719 is incident on the boundary between the auxiliary refraction part 719 and the main passage portion P2 at an incident angle Ab and is refracted at a refraction angle Ac. The light beam LR traveling in the main passage portion P2 is incident on the boundary between the main passage portion P2 and the second surface 721b at an incident angle Ac, and is refracted at a refraction angle Ad. Since the medium filling the main passage portion P2 and the medium filling the auxiliary passage portion P3 are equal to each other, the incident angle Aa becomes equal to the refraction angle Ac, and consequently the incident angle Aa becomes equal to the incident angle Ac. By providing the auxiliary refraction part 719, it is possible to freely position the indication part 731 relative to the second surface 721*b* while exhibiting the display function in the first state and the second state and to reduce the volume of the passage (the volume of the main passage portion and the auxiliary passage portion).

The refractive $n_r'$ of the auxiliary refraction part 719 may be equal to the refractive index $n_r$ of the refraction part 720. The refractive index n' of the auxiliary refraction part 719 may be greater than the refractive index $n_p$ of the priming liquid. When the refractive index $n_r$ is 1.333, the refractive $n_r'$ is greater than 1.333. Since the refractive index $n_r$ is greater than the refractive index $n_p$, it is possible to move the portion on which the image of the indication part 731 is focused in the leftward direction L when viewed in the observation direction V in the second state.

FIG. 11 is a conceptual cross-sectional view obtained by horizontally cutting a refraction part 720' according to another embodiment. The internal angle θ in the refraction part 720 in FIGS. 9A to 10 is 60 degrees. However, referring to FIG. 11, the internal angle θ of the refraction part 720' is smaller than 60 degrees. When the range of the above-described internal angle θ is satisfied, the size of the internal angle θ may be smaller than 60 degrees or greater than 60 degrees. FIG. 11 merely illustrates any one of various embodiment of the interior angle θ.

FIG. 12 is a conceptual cross-sectional view obtained by horizontally cutting a refraction part 720" according to still another embodiment. The first surface 721*a* and the second surface 721*b* form an internal angle θ. Referring to FIGS. 9A to 10, the first surface 721*a* and the second surface 721*b* form an edge and meet to form the internal angle θ. Referring to FIG. 12, an imaginary extension plane of the first surface 721*a* and an imaginary extension plane of the second surface 721*b* form the interior angle θ. That is, the description "the first surface 721*a* and the second surface 721*b* form the internal angle θ " covers not only the case in which the first surface 721*a* and the second surface 721*b* form an edge, but also the case in which the imaginary extension plane of the first surface 721*a* and the imaginary extension plane of the second surface 721*b* form the internal angle θ.

Although the technical idea of the present disclosure has been described above with reference to some embodiments and examples illustrated in the accompanying drawings, it should be understood that various substitutions, changes, and alterations can be made without departing from the technical idea and scope of the present disclosure. It should also be understood that such substitutions, modifications and variations are intended to fall within the scope of the present disclosure that is defined in the accompanying claims.

The invention claimed is:

1. An end cap connected to a downstream side of a flow path of a medical liquid injection apparatus such that a priming liquid is introduced into the end cap, the end cap comprising:
 a refraction part formed of a transparent material having a refractive index ($n_r$) greater than 1 and including a first surface and a second surface forming an internal angle (θ) smaller than 90 degrees; and
 an indication part disposed to be spaced apart from the second surface,
 wherein the end cap forms a passage in which the introduced priming liquid is movable,
 wherein a part of the passage is located between the second surface and the indication part,
 wherein the refraction part is configured such that, in a first state in which the passage is filled with air, all light that starts from the indication part travels in a direction different from a display direction, which is an outward direction perpendicular to the first surface, and, in a second state in which the passage is filled with the priming liquid, a part of light that starts from the indication part travels in the display direction,
 wherein a transparent portion is formed in the end cap to transmit light traveling in the display direction to an outside, and
 wherein a blind portion is formed in the end cap to block, scatter, or transmit, with transparency lower than transparency of the transparent portion, light passing through an area, other than an area corresponding to the transparent portion, in a peripheral surface of the refraction part including the first surface and the second surface.

2. The end cap of claim 1, wherein the refraction part is configured such that, in the first state, light totally reflected from the second surface travels in the display direction and, in the second state, a part of light that starts from the indication part is refracted on the second surface so as to travel in the display direction.

3. The end cap of claim 1, wherein the transparent portion is configured to correspond to a specific area in the first surface, and
 the specific area is located in a direction of the internal angle θ that the first surface forms with the second surface with respect to an area, other than the specific area, in the first surface.

4. The end cap of claim 1, wherein the internal angle (θ) is equal to or greater than $$\sin^{-1}\left(\frac{1}{n_r}\right).$$

5. The end cap of claim 1, wherein, when the priming liquid has a refractive index ($n_p$), the refractive index ($n_r$) is equal to or greater than $$\frac{1}{\sin\theta}$$

and smaller than $$\frac{n_p}{\sin\theta}.$$

6. The end cap of claim 1, wherein the refractive index ($n_r$) is equal to or greater than $$\frac{1}{\sin\theta}$$

and smaller than $$\frac{1.333}{\sin\theta}.$$

7. The end cap of claim 1, further comprising:
an auxiliary refraction part formed of a transparent material having a refractive index ($n_r'$) greater than 1 and located between the second surface and the indication part, the auxiliary refraction part being disposed to be spaced apart from the second surface, and
a part of the passage is located between the second surface and the auxiliary refraction part.

8. The end cap of claim 7, wherein the refractive index ($n_r'$) is greater than 1.333.

9. The end cap of claim 1, further comprising:
a casing part having an inlet port configured to allow the liquid to be introduced into the end cap therethrough from the flow path, and an outlet port configured to allow air to flow out from an inside of the passage therethrough,
wherein the refraction part is disposed inside the casing part.

10. The end cap of claim 9, wherein a surface, other than the second surface, in a peripheral surface of the refraction part comprising the first surface and the second surface, is in contact with an inner surface of the casing part.

11. The end cap of claim 1, further comprising:
a liquid absorption part disposed in a downstream side of a part of the passage located between the second surface and the indication part, the liquid absorption part being configured to absorb the liquid and having a shape corresponding to a shape of a downstream surface of the refraction part; and
a hydrophobic filter part disposed on a downstream side of the liquid absorption part, and configured to allow air to pass therethrough.

12. A medical liquid injection apparatus set comprising:
a pumping module configured to pressurize a medical liquid;
a connection flow path connected to the pumping module on an upstream side thereof and configured to guide a flow of a priming liquid; and
an end cap connected to a downstream side of the connection flow path and configured such that the priming liquid is introduced into the end cap,
wherein the end cap comprises:
a refraction part formed of a transparent material having a refractive index ($n_r$) greater than 1 and including a first surface and a second surface that form an internal angle ($\theta$) smaller than 90 degrees; and
an indication part disposed to be spaced apart from the second surface, and
wherein the end cap forms a passage in which the introduced priming liquid is movable,
wherein a part of the passage is located between the second surface and the indication part,
wherein the refraction part is configured such that, in a first state in which the passage is filled with air, all light that starts from the indication part travels in a direction different from a display direction, which is an outward direction perpendicular to the first surface, and, in a second state in which the passage is filled with the priming liquid, a part of light that starts from the indication part travels in the display direction,
wherein a transparent portion is formed in the end cap to transmit light traveling in the display direction to an outside, and
wherein a blind portion is formed in the end cap to block, scatter, or transmit, with transparency lower than transparency of the transparent portion, light passing through an area, other than an area corresponding to the transparent portion, in a peripheral surface of the refraction part including the first surface and the second surface.

* * * * *